United States Patent
Fong et al.

(10) Patent No.: US 6,348,351 B1
(45) Date of Patent: *Feb. 19, 2002

(54) TIE RECEPTOR TYROSINE KINASE LIGAND HOMOLOGUES

(75) Inventors: Sherman Fong, Alameda; Napoleone Ferrara; Audrey Goddard, both of San Francisco; Paul J. Godowski, Burlingame; Austin L. Gurney, Belmont; Kenneth Hillan, San Francisco; P. Mickey Williams, Half Moon Bay, all of CA (US)

(73) Assignee: Genentech, Inc., South SanFrancisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/202,089

(22) PCT Filed: Sep. 14, 1998

(86) PCT No.: PCT/US98/19094

§ 371 Date: Dec. 8, 1998

§ 102(e) Date: Dec. 8, 1998

(87) PCT Pub. No.: WO99/15654

PCT Pub. Date: Apr. 1, 1999

Related U.S. Application Data

(63) Continuation-in-part of application No. 08/934,494, filed on Sep. 19, 1997, now Pat. No. 6,030,831.

(51) Int. Cl.$^7$ .................. C07K 14/475; C12N 5/10; C12N 15/12
(52) U.S. Cl. .............. 435/325; 536/23.1; 536/23.5; 530/350; 435/69.1; 435/320.1; 435/252.3; 435/254.11
(58) Field of Search ............... 530/350, 300; 536/23.1, 23.5, 23.4; 435/69.1, 320.1, 252.3, 325, 254.11

(56) References Cited

U.S. PATENT DOCUMENTS

| | | |
|---|---|---|
| 5,447,860 A | 9/1995 | Ziegler |
| 5,521,073 A | 5/1996 | Davis et al. |
| 5,643,755 A | 7/1997 | Davis et al. |
| 5,650,490 A | 7/1997 | Davis et al. |
| 5,972,338 A | * 10/1999 | Godowski et al. |
| 6,030,831 A | * 2/2000 | Godowski et al. |

FOREIGN PATENT DOCUMENTS

| | | |
|---|---|---|
| WO | WO 93/14124 | 7/1993 |
| WO | WO 95/13387 | 5/1995 |
| WO | WO 95/21866 | 8/1995 |
| WO | WO 95/26364 | 10/1995 |
| WO | WO 96/09381 | 3/1996 |
| WO | WO 96/11269 | 4/1996 |
| WO | WO 96/31598 | 10/1996 |
| WO | WO 97/48804 | 12/1997 |
| WO | WO 98/05779 | 2/1998 |

OTHER PUBLICATIONS

Davis et al., "Isolation of Angiopoietin–1, a Ligand for the TIE2 Receptor, by Secretion—Trap Expression Cloning," *Cell*, 87:1161–1169 (1996).

Dumont et al., "The endothelial–specific receptor tyrosine kinase, tek, is a member of a new subfamily of receptors," *Oncogene* 8: 1293–1301 (1993).

Hanahan, D., "Signaling vascular morphogenesis and maintenance" *Science* 277:48–50 (1997).

Kaipainen et al., "Enhanced Expression of the Tie Receptor Tyrosine Kinase Messenger RNA in the Vascular Endothelium of Metastatic Melanomas," *Cancer Res.* 54:6571–6577 (1994).

Korhonen et al., "Enhanced Expression of the tie Receptor Tyrosine Kinase in Endothelial Cells During Neovascularization," *Blood* 80: 2548–2555 (1992).

Maisonpierre et al., "Distinct rat genes with related profiles of expression define a TIE receptor tyrosine kinase family," *Oncogene* 8:1631–1637 (1993).

Partanen et al., "Putative Tyrosine Kinases Expressed in K–562 Human Leukemia Cells", *Proc. Natl. Acad. Sci.*, 87:8913–8917 (1990).

Sugimoto et al., "Cloning and Characterization of the Hakata Antigen, a Member of the Ficolin/Opsonin p35 Lectin Family" Journal of Biological Chemistry 273 (33):20721–20727 (Aug. 14, 1998).

Suri et al., "Requisite Role of Angiopoietin–1, a Ligand for the TIE2 Receptor, during Embryonic Angiogenesis," *Cell*, 87:1171–1180 (1996).

Maisonpierre et al., "Angiopoietin–2, a Natural Antagonist for Tie2 that Disrupts in vivo Angiogenesis" *Science* 277: 55–60 (Jul. 4, 1997).

Marra et al., GenBank Accession No. AA243953, accessed Jan. 6, 1999.

BLAST Results A1–A2 (Alignment of DNA 22780 (encoding NL2) and various EST sequences—GenBank Database).

BLAST Results B1–B2 (Alignment of DNA 33457 (encoding NL3) and various EST sequences—GenBank database).

BLAST Results C1–C2 (Sequence Comparison of NL2 and FLS139—Dayhoff database).

* cited by examiner

*Primary Examiner*—Lorraine Spector
*Assistant Examiner*—Claire M. Kaufman
(74) *Attorney, Agent, or Firm*—Knobbe, Martens, Olson & Bear, LLP

(57) ABSTRACT

The present invention concerns isolated nucleic acid molecules encoding the novel TIE ligand homologues NL2, NL3 and NL6 (FLS139), the proteins encoded by such nucleic acid molecules, as well as methods and means for making and using such nucleic acid and protein molecules.

10 Claims, 14 Drawing Sheets

SEQ ID NO:1:

| | | | | |
|---|---|---|---|---|
| GCCGAGCTGA | GCGGATCCTC | ACATGACTGT | GATCCGATTC | TTTCCAGCGG 50 |
| CTTCTGCAAC | CAAGCGGGTC | TTACCCCCGG | TCCTCCGCGT | CTCCAGTCCT 100 |
| CGCACCTGGA | ACCCCAACGT | CCCCGAGAGT | CCCCGAATCC | CCGCTCCCAG 150 |
| GCTACCTAAG | AGGATGAGCG | GTGCTCCGAC | GGCCGGGGCA | GCCCTGATGC 200 |
| TCTGCCGC | CACCGCCGTG | CTACTGAGCG | CTCAGGGCGG | ACCCGTGCAG 250 |
| TCCAAGTCGC | CGCGCTTTGC | GTCCTGGGAC | GAGATGAATG | TCCTGGCGCA 300 |
| CGGACTCCTG | CAGCTCGGCC | AGGGGCTGCG | CGAACACGCG | GAGCGCACCC 350 |
| GCAGTCAGCT | GAGCGCGCTG | GAGCGGCGCC | TGAGCGCGTG | CGGGTCCGCC 400 |
| TGTCAGGGAA | CCGAGGGGTC | CACCGACCTC | CCGTTAGCCC | CTGAGAGCCG 450 |
| GGTGGACCCT | GAGGTCCTTC | ACAGCCTGCA | GACACAACTC | AAGGCTCAGA 500 |
| ACAGCAGGAT | CCAGCAACTC | TTCCACAAGG | TGGCCCAGCA | GCAGCGGCAC 550 |
| CTGGAGAAGC | AGCACCTGCG | AATTCAGCAT | CTGCAAAGCC | AGTTTGGCCT 600 |
| CCTGGACCAC | AAGCACCTAG | ACCATGAGGT | GGCCAAGCCT | GCCCGAAGAA 650 |
| AGAGGCTGCC | CGAGATGGCC | CAGCCAGTTG | ACCCGGCTCA | CAATGTCAGC 700 |
| CGCCTGCACC | GGCTGCCCAG | GGATTGCCAG | GAGCTGTTCC | AGGTTGGGGA 750 |
| GAGGCAGAGT | GGACTATTTG | AAATCCAGCC | TCAGGGTCT | CCGCCATTTT 800 |
| TGGTGAACTG | CAAGATGACC | TCAGATGGAG | GCTGGACAGT | AATTCAGAGG 850 |
| CGCCACGATG | GCTCAGTGGA | CTTCAACCGG | CCCTGGGAAG | CCTACAAGGC 900 |
| GGGGTTTGGG | GATCCCCACG | GCGAGTTCTG | GCTGGGTCTG | GAGAAGGTGC 950 |
| ATAGCATCAC | GGGGGACCGC | AACAGCCGCC | TGGCCGTGCA | GCTGCGGGAC 1000 |
| TGGGATGGCA | ACGCCGAGTT | GCTGCAGTTC | TCCGTGCACC | TGGGTGGCGA 1050 |
| GGACACGGCC | TATAGCCTGC | AGCTCACTGC | ACCCGTGGCC | GGCCAGCTGG 1100 |
| GCGCCACCAC | CGTCCCACCC | AGCGGCCTCT | CCGTACCCTT | CTCCACTTGG 1150 |

FIG. 2A

```
GACCAGGATC ACGACCTCCG CAGGGACAAG AACTGCGCCA AGAGCCTCTC 1200

TGGAGGCTGG TGGTTTGGCA CCTGCAGCCA TTCCAACCTC AACGGCCAGT 1250

ACTTCCGCTC CATCCCACAG CAGCGGCAGA AGCTTAAGAA GGGAATCTTC 1300

TGGAAGACCT GGCGGGGCCG CTACTACCCG CTGCAGGCCA CCACCATGTT 1350

GATCCAGCCC ATGGCAGCAG AGGCAGCCTC CTAGCGTCCT GGCTGGGCCT 1400

GGTCCCAGGC CCACGAAAGA CGGTGACTCT TGGCTCTGCC CGAGGATGTG 1450

GCCGTTCCCT GCCTGGGCAG GGGCTCCAAG GAGGGGCCAT CTGGAAACTT 1500

GTGGACAGAG AAGAAGACCA CGACTGGAGA AGCCCCCTTT CTGAGTGCAG 1550

GGGGGCTGCA TGCGTTGCCT CCTGAGATCG AGGCTGCAGG ATATGCTCAG 1600

ACTCTAGAGG CGTGGACCAA GGGGCATGGA GCTTCACTCC TTGCTGGCCA 1650

GGGAGTTGGG GACTCAGAGG GACCACTTGG GGCCAGCCAG ACTGGCCTCA 1700

ATGGCGGACT CAGTCACATT GACTGACGGG GACCAGGGCT TGTGTGGGTC 1750

GAGAGCGCCC TCATGGTGCT GGTGCTGTTG TGTGTAGGTC CCTGGGGAC 1800

ACAAGCAGGC GCCAATGGTA TCTGGGCGGA GCTCACAGAG TTCTTGGAAT 1850

AAAAGCAACC TCAGAACAC 1869
```

FIG. 2B

SEQ ID NO:2:

| | | | | | | | | | | | | | | |
|---|---|---|---|---|---|---|---|---|---|---|---|---|---|---|
| Met | Ser | Gly | Ala | Pro | Thr | Ala | Gly | Ala | Ala | Leu | Met | Leu | Cys | Ala |
| 1 | | | | 5 | | | | | 10 | | | | | 15 |
| Ala | Thr | Ala | Val | Leu | Leu | Ser | Ala | Gln | Gly | Gly | Pro | Val | Gln | Ser |
| | | | | 20 | | | | | 25 | | | | | 30 |
| Lys | Ser | Pro | Arg | Phe | Ala | Ser | Trp | Asp | Glu | Met | Asn | Val | Leu | Ala |
| | | | | 35 | | | | | 40 | | | | | 45 |
| His | Gly | Leu | Leu | Gln | Leu | Gly | Gln | Gly | Leu | Arg | Glu | His | Ala | Glu |
| | | | | 50 | | | | | 55 | | | | | 60 |
| Arg | Thr | Arg | Ser | Gln | Leu | Ser | Ala | Leu | Glu | Arg | Arg | Leu | Ser | Ala |
| | | | | 65 | | | | | 70 | | | | | 75 |
| Cys | Gly | Ser | Ala | Cys | Gln | Gly | Thr | Glu | Gly | Ser | Thr | Asp | Leu | Pro |
| | | | | 80 | | | | | 85 | | | | | 90 |
| Leu | Ala | Pro | Glu | Ser | Arg | Val | Asp | Pro | Glu | Val | Leu | His | Ser | Leu |
| | | | | 95 | | | | | 100 | | | | | 105 |
| Gln | Thr | Gln | Leu | Lys | Ala | Gln | Asn | Ser | Arg | Ile | Gln | Gln | Leu | Phe |
| | | | | 110 | | | | | 115 | | | | | 120 |
| His | Lys | Val | Ala | Gln | Gln | Arg | His | Leu | Glu | Lys | Gln | His | Leu | |
| | | | | 125 | | | | | 130 | | | | | 135 |
| Arg | Ile | Gln | His | Leu | Gln | Ser | Gln | Phe | Gly | Leu | Leu | Asp | His | Lys |
| | | | | 140 | | | | | 145 | | | | | 150 |
| His | Leu | Asp | His | Glu | Val | Ala | Lys | Pro | Ala | Arg | Arg | Lys | Arg | Leu |
| | | | | 155 | | | | | 160 | | | | | 165 |
| Pro | Glu | Met | Ala | Gln | Pro | Val | Asp | Pro | Ala | His | Asn | Val | Ser | Arg |
| | | | | 170 | | | | | 175 | | | | | 180 |
| Leu | His | Arg | Leu | Pro | Arg | Asp | Cys | Gln | Glu | Leu | Phe | Gln | Val | Gly |
| | | | | 185 | | | | | 190 | | | | | 195 |
| Glu | Arg | Gln | Ser | Gly | Leu | Phe | Glu | Ile | Gln | Pro | Gln | Gly | Ser | Pro |
| | | | | 200 | | | | | 205 | | | | | 210 |
| Pro | Phe | Leu | Val | Asn | Cys | Lys | Met | Thr | Ser | Xaa | Gly | Gly | Trp | Thr |
| | | | | 215 | | | | | 220 | | | | | 225 |
| Val | Ile | Gln | Arg | Arg | His | Asp | Gly | Ser | Val | Asp | Phe | Asn | Arg | Pro |
| | | | | 230 | | | | | 235 | | | | | 240 |

FIG. 3A

Trp Glu Ala Tyr Lys Ala Gly Phe Gly Asp Pro His Gly Glu Phe
            245             250             255

Trp Leu Gly Leu Glu Lys Val His Ser Ile Thr Gly Asp Arg Asn
            260             265             270

Ser Arg Leu Ala Val Gln Leu Arg Asp Trp Asp Gly Asn Ala Glu
            275             280             285

Leu Leu Gln Phe Ser Val His Leu Gly Gly Glu Asp Thr Ala Tyr
            290             295             300

Ser Leu Gln Leu Thr Ala Pro Val Ala Gly Gln Leu Gly Ala Thr
            305             310             315

Thr Val Pro Pro Ser Gly Leu Ser Val Pro Phe Ser Thr Trp Asp
            320             325             330

Gln Asp His Asn Leu Arg Arg Asp Lys Asn Cys Ala Lys Ser Leu
            335             340             345

Ser Gly Gly Trp Trp Phe Gly Thr Cys Ser His Ser Asn Leu Asn
            350             355             360

Gly Gln Tyr Phe Arg Ser Ile Pro Gln Gln Arg Gln Lys Leu Lys
            365             370             375

Lys Gly Ile Phe Trp Lys Thr Trp Arg Gly Arg Tyr Tyr Pro Leu
            380             385             390

Gln Ala Thr Thr Met Leu Ile Gln Pro Met Ala Ala Glu Ala Ala
            395             400             405

Ser
406

FIG. 3B

SEQ ID NO:3:

```
CGGACGCGTG GGCCCCTGGT GGGCCCAGCA AGATGGATCT ACTGTGGATC   50
CTGCCCTCCC TGTGGCTTCT CCTGCTTGGG GGGCCTGCCT GCCTGAAGAC  100
CCAGGAACAC CCCAGCTGCC CAGGACCCAG GAACTGGAA  GCCAGCAAAG  150
TTGTCCTCCT GCCCAGTTGT CCCGGAGCTC CAGGAAGTCC TGGGGAGAAG  200
GGAGCCCCAG GTCCTCAAGG GCCACCTGGA CCACCAGGCA AGATGGGCCC  250
CAAGGGTGAG CCAGGCCCCA GAAACTGCCG GGAGCTGTTG AGCCAGGGCG  300
CCACCTTGAG CGGCTGGTAC CATCTGTGCC TACCTGAGGG CAGGGCCCTC  350
CCAGTCTTTT GTGACATGGA CACCGAGGGG GGCGGCTGGC TGGTGTTTCA  400
GAGGCGCCAG GATGGTTCTG TGGATTTCTT CCGCTCTTGG TCCTCCTACA  450
GAGCAGGTTT TGGGAACCAA GAGTCTGAAT TCTGGCTGGG AAATGAGAAT  500
TTGCACCAGC TTACTCTCCA GGGTAACTGG GAGCTGCGGG TAGAGCTGGA  550
AGACTTTAAT GGTAACCGTA CTTTCGCCCA CTATGCGACC TTCCGCCTCC  600
TCGGTGAGGT AGACCACTAC CAGCTGGCAC TGGGCAAGTT CTCAGAGGGC  650
ACTGCAGGGG ATTCCCTGAG CCTCCACAGT GGGAGGCCCT TTACCACCTA  700
TGACGCTGAC CACGATTCAA GCAACAGCAA CTGTGCAGTG ATTGTCCACG  750
GTGCCTGGTG GTATGCATCC TGTTACCGAT CAAATCTCAA TGGTCGCTAT  800
GCAGTGTCTG AGGCTGCCGC CCACAAATAT GGCATTGACT GGGCCTCAGG  850
CCGTGGTGTG GGCCACCCCT ACCGCAGGGT TCGGATGATG CTTCGATAGG  900
GCACTCTGGC AGCCAGTGCC CTTATCTCTC CTGTACAGCT TCCGGATCGT  950
CAGCCACCTT GCCTTTGCCA ACCACCTCTG CTTGCCTGTC CACATTTAAA 1000
AATAAAATCA TTTTAGCCCT TTCA                             1024
```

FIG. 4

SEQ ID NO:4:

```
Met Asp Leu Leu Trp Ile Leu Pro Ser Leu Trp Leu Leu Leu Leu
 1           5                       10                   15

Gly Gly Pro Ala Cys Leu Lys Thr Gln Glu His Pro Ser Cys Pro
                20                  25                   30

Gly Pro Arg Glu Leu Glu Ala Ser Lys Val Val Leu Leu Pro Ser
                35                  40                   45

Cys Pro Gly Ala Pro Gly Ser Pro Gly Glu Lys Gly Ala Pro Gly
                50                  55                   60

Pro Gln Gly Pro Pro Gly Pro Pro Gly Lys Met Gly Pro Lys Gly
                65                  70                   75

Glu Pro Gly Pro Arg Asn Cys Arg Glu Leu Leu Ser Gln Gly Ala
                80                  85                   90

Thr Leu Ser Gly Trp Tyr His Leu Cys Leu Pro Glu Gly Arg Ala
                95                 100                  105

Leu Pro Val Phe Cys Asp Met Asp Thr Glu Gly Gly Gly Trp Leu
               110                 115                  120

Val Phe Gln Arg Arg Gln Asp Gly Ser Val Asp Phe Phe Arg Ser
               125                 130                  135

Trp Ser Ser Tyr Arg Ala Gly Phe Gly Asn Gln Glu Ser Glu Phe
               140                 145                  150

Trp Leu Gly Asn Glu Asn Leu His Gln Leu Thr Leu Gln Gly Asn
               155                 160                  165

Trp Glu Leu Arg Val Glu Leu Glu Asp Phe Asn Gly Asn Arg Thr
               170                 175                  180

Phe Ala His Tyr Ala Thr Phe Arg Leu Leu Gly Glu Val Asp His
               185                 190                  195

Tyr Gln Leu Ala Leu Gly Lys Phe Ser Glu Gly Thr Ala Gly Asp
               200                 205                  210

Ser Leu Ser Leu His Ser Gly Arg Pro Phe Thr Thr Tyr Asp Ala
               215                 220                  225

Asp His Asp Ser Ser Asn Ser Asn Cys Ala Val Ile Val His Gly
               230                 235                  240

Ala Trp Trp Tyr Ala Ser Cys Tyr Arg Ser Asn Leu Asn Gly Arg
               245                 250                  255

Tyr Ala Val Ser Glu Ala Ala Ala His Lys Tyr Gly Ile Asp Trp
               260                 265                  270

Ala Ser Gly Arg Gly Val Gly His Pro Tyr Arg Arg Val Arg Met
               275                 280                  285

Met Leu Arg
   288
```

FIG. 5

SEQ ID NO:5:

```
GCGGACGCGT GGGTGAAATT GAAAATCAAG ATAAAAATGT TCACAATTAA   50
GCTCCTTCTT TTTATTGTTC CTCTAGTTAT TTCCTCCAGA ATTGATCAAG  100
ACAATTCATC ATTTGATTCT CTATCTCCAG AGCCAAAATC AAGATTTGCT  150
ATGTTAGACG ATGTAAAAAT TTTAGCCAAT GGCCTCCTTC AGTTGGGACA  200
TGGTCTTAAA GACTTTGTCC ATAAGACGAA GGGCCAAATT AATGACATAT  250
TTCAAAAACT CAACATATTT GATCAGTCTT TTTATGATCT ATCGCTGCAA  300
ACCAGTGAAA TCAAGAAGA AGAAAAGGAA CTGAGAAGAA CTACATATAA   350
ACTACAAGTC AAAAATGAAG AGGTAAAGAA TATGTCACTT GAACTCAACT  400
CAAAACTTGA AAGCCTCCTA GAAGAAAAAA TTCTACTTCA ACAAAAGTG   450
AAATATTTAG AAGAGCAACT AACTAACTTA ATTCAAAATC AACCTGAAAC  500
TCCAGAACAC CCAGAAGTAA CTTCACTTAA AACTTTTGTA GAAAAACAAG  550
ATAATAGCAT CAAAGACCTT CTCCAGACCG TGGAAGACCA ATATAAACAA  600
TTAAACCAAC AGCATAGTCA AATAAAAGAA ATAGAAAATC AGCTCAGAAG  650
GACTAGTATT CAAGAACCCA CAGAAATTTC TCTATCTTCC AAGCCAAGAG  700
CACCAAGAAC TACTCCCTTT CTTCAGTTGA ATGAAATAAG AAATGTAAAA  750
CATGATGGCA TTCCTGCTGA ATGTACCACC ATTTATAACA GAGGTGAACA  800
TACAAGTGGC ATGTATGCCA TCAGACCCAG CAACTCTCAA GTTTTTCATG  850
TCTACTGTGA TGTTATATCA GGTAGTCCAT GGACATTAAT TCAACATCGA  900
ATAGATGGAT CACAAAACTT CAATGAAACG TGGGAGAACT ACAAATATGG  950
TTTTGGGAGG CTTGATGGAG AATTTGGTT GGGCCTAGAG AAGATATACT  1000
CCATAGTGAA GCAATCTAAT TATGTTTTAC GAATTGAGTT GGAAGACTGG  1050
AAAGACAACA AACATTATAT TGAATATTCT TTTTACTTGG AAATCACGA   1100
AACCAACTAT ACGCTACATC TAGTTGCGAT TACTGGCAAT GTCCCCAATG  1150
```

FIG. 6A

```
CAATCCCGGA AAACAAAGAT TTGGTGTTTT CTACTTGGGA TCACAAAGCA 1200
AAAGGACACT TCAACTGTCC AGAGGGTTAT TCAGGAGGCT GGTGGTGGCA 1250
TGATGAGTGT GGAGAAAACA ACCTAAATGG TAAATATAAC AAACCAAGAG 1300
CAAAATCTAA GCCAGAGAGG AGAAGAGGAT TATCTTGGAA GTCTCAAAAT 1350
GGAAGGTTAT ACTCTATAAA ATCAACCAAA ATGTTGATCC ATCCAACAGA 1400
TTCAGAAAGC TTTGAATGAA CTGAGGCAAT TTAAAGGCAT ATTTAACCAT 1450
TAACTCATTC CAAGTTAATG TGGTCTAATA ATCTGGTATA AATCCTTAAG 1500
AGAAAGCTTG AGAAATAGAT TTTTTTTATC TTAAAGTCAC TGTCTATTTA 1550
AGATTAAACA TACAATCACA TAACCTTAAA GAATACCGTT TACATTTCTC 1600
AATCAAAATT CTTATAATAC TATTTGTTTT AAATTTTGTG ATGTGGGAAT 1650
CAATTTTAGA TGGTCACAAT CTAGATTATA ATCAATAGGT GAACTTATTA 1700
AATAACTTTT CTAAATAAAA AATTTAGAGA CTTTTATTTT AAAAGGCATC 1750
ATATGAGCTA ATATCACAAC TTTCCCAGTT TAAAAAACTA GTACTCTTGT 1800
TAAAACTCTA AACTTGACTA AATACAGAGG ACTGGTAATT GTACAGTTCT 1850
TAAATGTTGT AGTATTAATT TCAAAACTAA AAATCGTCAG CACAGAGTAT 1900
GTGTAAAAAT CTGTAATACA AATTTTTAAA CTGATGCTTC ATTTTGCTAC 1950
AAAATAATTT GGAGTAAATG TTTGATATGA TTTATTTATG AAACCTAATG 2000
AAGCAGAATT AAATACTGTA TTAAAATAAG TTCGCTGTCT TT 2042
```

FIG. 6B

SEQ ID NO:6:

```
Met Phe Thr Ile Lys Leu Leu Leu Phe Ile Val Pro Leu Val Ile
 1               5                  10                  15

Ser Ser Arg Ile Asp Gln Asp Asn Ser Ser Phe Asp Ser Leu Ser
                20                  25                  30

Pro Glu Pro Lys Ser Arg Phe Ala Met Leu Asp Asp Val Lys Ile
                35                  40                  45

Leu Ala Asn Gly Leu Leu Gln Leu Gly His Gly Leu Lys Asp Phe
                50                  55                  60

Val His Lys Thr Lys Gly Gln Ile Asn Asp Ile Phe Gln Lys Leu
                65                  70                  75

Asn Ile Phe Asp Gln Ser Phe Tyr Asp Leu Ser Leu Gln Thr Ser
                80                  85                  90

Glu Ile Lys Glu Glu Glu Lys Glu Leu Arg Arg Thr Thr Tyr Lys
                95                  100                 105

Leu Gln Val Lys Asn Glu Glu Val Lys Asn Met Ser Leu Glu Leu
                110                 115                 120

Asn Ser Lys Leu Glu Ser Leu Leu Glu Glu Lys Ile Leu Leu Gln
                125                 130                 135

Gln Lys Val Lys Tyr Leu Glu Glu Gln Leu Thr Asn Leu Ile Gln
                140                 145                 150

Asn Gln Pro Glu Thr Pro Glu His Pro Glu Val Thr Ser Leu Lys
                155                 160                 165

Thr Phe Val Glu Lys Gln Asp Asn Ser Ile Lys Asp Leu Leu Gln
                170                 175                 180

Thr Val Glu Asp Gln Tyr Lys Gln Leu Asn Gln Gln His Ser Gln
                185                 190                 195

Ile Lys Glu Ile Glu Asn Gln Leu Arg Arg Thr Ser Ile Gln Glu
                200                 205                 210

Pro Thr Glu Ile Ser Leu Ser Ser Lys Pro Arg Ala Pro Arg Thr
                215                 220                 225

Thr Pro Phe Leu Gln Leu Asn Glu Ile Arg Asn Val Lys His Asp
                230                 235                 240
```

FIG. 7A

```
Gly Ile Pro Ala Glu Cys Thr Thr Ile Tyr Asn Arg Gly Glu His
                245             250                 255

Thr Ser Gly Met Tyr Ala Ile Arg Pro Ser Asn Ser Gln Val Phe
                260             265                 270

His Val Tyr Cys Asp Val Ile Ser Gly Ser Pro Trp Thr Leu Ile
                275             280                 285

Gln His Arg Ile Asp Gly Ser Gln Asn Phe Asn Glu Thr Trp Glu
                290             295                 300

Asn Tyr Lys Tyr Gly Phe Gly Arg Leu Asp Gly Glu Phe Trp Leu
                305             310                 315

Gly Leu Glu Lys Ile Tyr Ser Ile Val Lys Gln Ser Asn Tyr Val
                320             325                 330

Leu Arg Ile Glu Leu Glu Asp Trp Lys Asp Asn Lys His Tyr Ile
                335             340                 345

Glu Tyr Ser Phe Tyr Leu Gly Asn His Glu Thr Asn Tyr Thr Leu
                350             355                 360

His Leu Val Ala Ile Thr Gly Asn Val Pro Asn Ala Ile Pro Glu
                365             370                 375

Asn Lys Asp Leu Val Phe Ser Thr Trp Asp His Lys Ala Lys Gly
                380             385                 390

His Phe Asn Cys Pro Glu Gly Tyr Ser Gly Gly Trp Trp Trp His
                395             400                 405

Asp Glu Cys Gly Glu Asn Asn Leu Asn Gly Lys Tyr Asn Lys Pro
                410             415                 420

Arg Ala Lys Ser Lys Pro Glu Arg Arg Arg Gly Leu Ser Trp Lys
                425             430                 435

Ser Gln Asn Gly Arg Leu Tyr Ser Ile Lys Ser Thr Lys Met Leu
                440             445                 450

Ile His Pro Thr Asp Ser Glu Ser Phe Glu
                455             460
```

FIG. 7B

TIE RECEPTOR TYROSINE KINASE LIGAND HOMOLOGUES

This application claims benefit of the filing date under 35 U.S.C. §120, as a CIP of U.S. application Ser. No. 08/934,494 filed on Sep. 19, 1997 now U.S. Pat. No. 6,030,831.

FIELD OF THE INVENTION

The present invention concerns isolated nucleic acid molecules encoding novel TIE ligand homologues, the TIE ligand homologueproteins encoded by such nucleic acid molecules, as well as methods and means for making and using such nucleic acid and protein molecules, and antibodies binding the disclosed TIE ligand homologues.

BACKGROUND

The abbreviations "TIE" or "tie" are acronyms, which stand for "tyrosine kinase containing Ig and EGF homology domains" and were coined to designate a new family ofreceptortyrosine kinases which are almost exclusively expressed in vascular endothelial cells and early hemopoietic cells, and are characterized by the presence of an EGF-like domain, and extracellular folding units stabilized by intra-chain disulfide bonds, generally referred to as "immunoglobulin (IG)-like" folds. A tyrosine kinase homologous cDNA fragment from human leukemia cells (tie) was described by Partanen et al., *Proc. Natl. Acad. Sci. USA* 87, 8913–8917 (1990). The mRNA of this human "tie" receptor has been detected in all human fetal and mouse embryonic tissues, and has been reported to be localized in the cardiac and vascular endothelial cells. Korhonenet al., *Blood* 80, 2548–2555 (1992); PCT Application Publication No. WO 93/14124 (published Jul. 22, 1993). The rat homolog of human tie, referred to as "tie-1", was identified by Maisonpierre et al., *Oncogene* 8, 1631–1637 (1993)). Another tie receptor, designated "tie-2" was originally identified in rats (Dumont et al., *Oncogene* 8, 1293–1301 (1993)), while the human homolog of tie-2, referred to as "ork" was described in U.S. Pat. No. 5,447,860 (Ziegler). The murine homolog of tie-2 was originally termed "tek." The cloning of a mouse tie-2 receptor from a brain capillary cDNA library is disclosed in PCT Application Publication No. WO 95/13387 (published May 18, 1995). The TIE receptors are believed to be actively involved in angiogenesis, and may play a role in hemopoiesis as well.

The expression cloning of human TIE-2 ligands has been described in PCT Application Publication No. WO 96/11269 (published Apr. 18, 1996) and in U.S. Pat. No. 5,521,073 (published May 28, 1996). A vector designated as λgt10 encoding a TIE-2 ligand named "htie-2 ligand 1" or "hTL1" has been deposited under ATCC Accession No. 75928. A plasmid encoding another TIE-2 ligand designated "htie-2 2" or "hTL2" is available under ATCC Accession No. 75928. This second ligand has been described as an antagonist of the TAI-2 receptor. The identification of secreted human and mouse ligands for the TIE-2 receptor has been reported by Davis et al., *Cell* 87, 1161–1169 (1996). The human ligand designated "Angiopoietin-1", to reflect its role in angiogenesis and potential action during hemopoiesis, is the same ligand as the ligand variously designated as "htie-2 1" or "hTL-1" in WO 96/11269. Angiopoietin-1 has been described to play an angiogenic role later and distinct from that of VEGF (Suri et al., *Cell* 87, 1171–1180(1996)). Since TIE-2 is apparently up regulated during the pathologic angiogenesis requisite for tumor growth (Kaipainen et al., *Cancer Res.* 54, 6571–6577 (1994)) angiopoietin-1 has been suggested to be additionally useful for specifically targeting tumor vasculature (Davis et al., supra).

SUMMARY OF THE INVENTION

The present invention concerns novel human TIE ligand homologues with powerful effects on vasculature. The invention also provides for isolated nucleic acid molecules encoding such ligand homologues or functional derivatives thereof, and vectors containing such nucleic acid molecules. The invention further concerns host cells transformed with such nucleic acid to produce the novel TIE ligand homologues or functional derivatives thereof. The novel ligand homologues may be agonists or antagonists of TIE receptors, known or hereinafter discovered. Their therapeutic or diagnostic use, including the delivery of other therapeutic or diagnostic agents to cells expressing the respective TIE receptors, is also within the scope of the present invention.

The present invention further provides for agon ist or antagonist antibodies specifically binding the TIE ligand homologues herein, and the diagnostic or therapeutic use of such antibodies.

In another aspect, the invention concerns compositions comprising the novel ligand homologues or antibodies.

In a further aspect, the invention concerns conjugates of the novel TIE ligand homologues of the present invention with other therapeutic or cytotoxic agents, and compositions comprising such conjugates. The TIE-2 receptor has been reported to be upregulated during the pathologic angiogenesis that is requisite for tumor growth, and other TIE receptors might have similar properties. Accordingly, the conjugates of the TIE ligand homologues of the present invention to cytotoxic or other anti-tumor agents may be useful in specifically targeting tumor vasculature.

In yet another aspect, the invention concerns a method for identifying a cell that expresses a TIE receptor, which comprises contacting a cell with a detectably labeled TIE ligand of homologue the present invention under conditions permitting the binding of such TIE ligand homologue to the TIE receptor, and determining whether such binding has indeed occurred.

In a different aspect, the invention concerns a method for measuring the amount of a TIE ligand homologue of the present invention in a biological sample by contacting the biological sample with at least one antibody specifically binding the TIE ligand homologue, and measuring the amount of the TIE ligand homologue-antibody complex formed.

The invention further concerns a screening method for identifying polypeptide or small molecule agonists or antagonists of a TIE receptor based upon their ability to compete with a native or variant TIE ligand homologue of the present invention for binding to a corresponding TIE receptor.

The invention also concerns a method for imaging the presence of angiogenesis in wound healing, in inflammation or in tumors of human patients, which comprises administering detectably labeled TIE ligand homologues or agonist antibodies of the present invention, and detecting angiogenesis.

In another aspect, the invention concerns a method of promoting or inhibiting neovascularization in a patient by administering an effective amount of a TIE ligand homologue of the present invention in a pharmaceutically acceptable vehicle. In a preferred embodiment, the present invention concerns a method for the promotion of wound healing. In another embodiment, the invention concerns a method for promoting angiogenic processes, such as for inducing collateral vascularization in an ischemic heart or limb.

In a further preferred embodiment, the invention concerns a method for inhibiting tumor growth.

In yet another aspect, the invention concerns a method of promoting bone development and/or maturation and/or growth in a patient, comprising administering to the patient an effective amount of a TIE ligand homologue of the present invention in a pharmaceutically acceptable vehicle.

In a further aspect, the invention concerns a method of promoting muscle growth and development, which comprises administering to a patient in need an effective amount of a TIE ligand homologue of the present invention in a pharmaceutically acceptable vehicle.

In yet another aspect, the invention concerns a method of inhibiting endothelial cell growth and/or inducing apoptosis of endothelial cells by administering an effective amount of a TIE ligand homologue of the present invention. In addition, the invention concerns a method of inhibiting inflammation, which comprises administering to a patient an effective amount of an antagonist of a TIE ligand homologue of the present invention, such as, an antibody to a TIE ligand homologue herein, e.g., an antagonist anti-NL6 antibody.

The TIE ligand homologues of the present invention may be administered alone, or in combination with each other and/or with other therapeutic or diagnostic agents, including members of the VEGF family. Combination therapies may lead to new approaches for promoting or inhibiting neovascularization, muscle and/or bone growth, development or differentiation, or treatment of conditions associated with unwanted endothelial cell growth, e.g. tumor treatment.

BRIEF DESCRIPTION OF THE FIGURES

FIG. 2 is the nucleotide sequence of the TIE ligand NL2 (SEQ. ID. NO: 1) (DNA 22780).

FIG. 3 is the amino acid sequence of the TIE ligand NL2 (SEQ. ID. NO:2).

FIG. 4 is the nucleotide sequence of the TIE ligand NL3 (SEQ. ID. NO: 3) (DNA 33457).

FIG. 5 is the amino acid sequence of the TIE ligand NL3 (SEQ. ID. NO: 4).

FIG. 6 is the nucleotide sequence of the TIE ligand FLS139 (SEQ. ID NO: 5) (DNA 16451).

FIG. 7 is the amino acid sequence of the TIE ligand FLS139 (SEQ. ID NO:6).

DETAILED DESCRIPTION OF THE INVENTION

Figure 1:
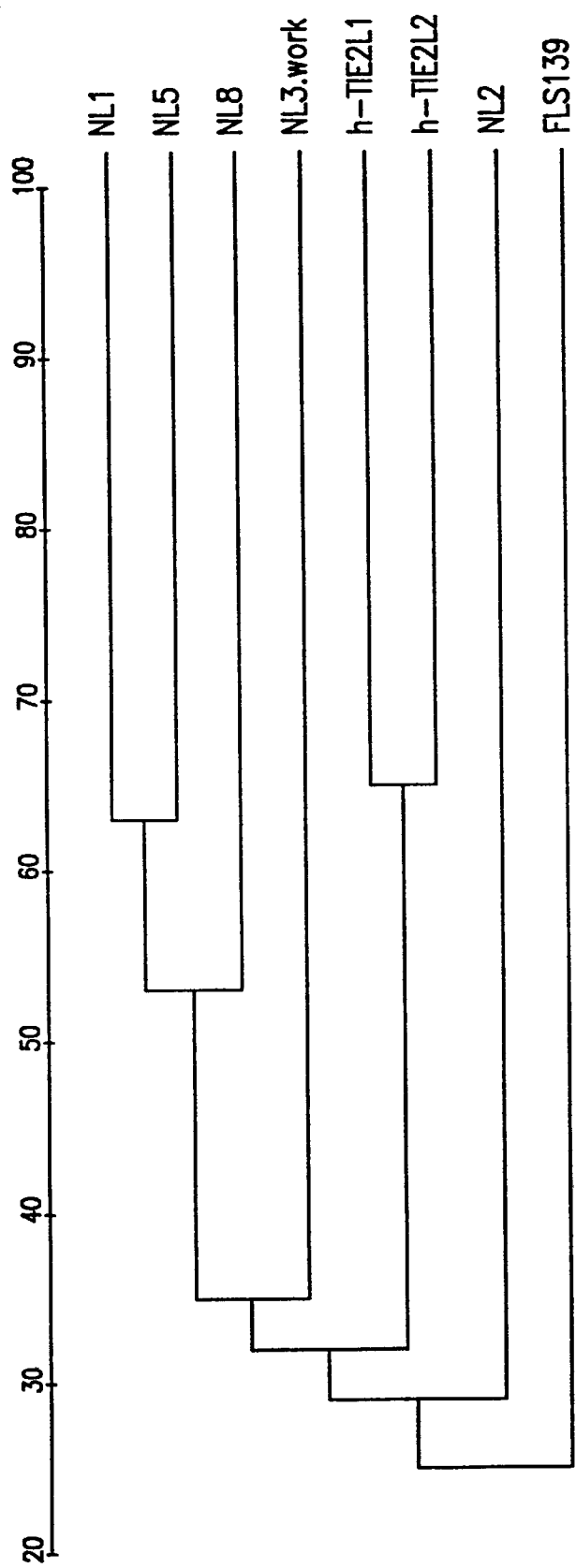
FIG. 1 is a graphic depiction of the relationship of the ligand homologues NL2, NL3 and FLS139 with the two known ligand homologues of the TIE2 receptor (h-TIE2L1 and h-TIE2L2) and with other TIE ligand homologues disclosed in application Ser. No. 08/933,821, filed on Sep. 19, 1997.

A. The Ligand Homologues and Nucleic Acid Molecules Encoding Them

The TIE ligand homologues of the present invention include the native human ligand homologues designated NL2 (SEQ. ID. NO: 2), NL3 (SEQ. ID. NO: 4), and FLS 139 (subsequently renamed as "NL6"; SEQ. ID. NO: 6), their homologs in other, non-human mammalian species, including, but not limited to, higher mammals, such as monkey; rodents, such as mice, rats, hamster; porcine; equine; bovine; naturally occurring allelic and splice variants, and biologically active (functional) derivatives, such as, amino acid sequence variants of such native molecules, as long as they differ from a native TL-1 or TL-2 ligand. Native NL2, as disclosed herein, has 27% amino acid sequence identity with hTL-1 (TIE2L1) and about 24% amino acid sequence identity with hTL-2 (TIE2L2). The amino acid sequence of native NL3, as disclosed herein, is about 30% identical with that of hTL-1 and about 29% identical with that of hTL-2. The amino acid sequence identity between native FLS139 (NL6), as disclosed herein, and hTL-1 and h-TL2 is about 21%. The native TIE ligand homologues of the present invention are substantially free of other proteins with which they are associated in their native environment. This definition is not limited in any way by the method(s) by which the TIE ligand homologues of the present invention are obtained, and includes all ligand homologues otherwise within the definition, whether purified from natural source, obtained by recombinant DNA technology, synthesized, or prepared by any combination of these andlor other techniques. The amino acid sequence variants of the native TIE ligand homologues of the present invention shall have at least about 90%, preferably, at least about 95%, more preferably at least about 98%, most preferably at least about 99% sequence identity with a full-length, native human TIE ligand homologue of the present invention, or with the fibrinogen-like domain of a native human TIE ligand homologue of the present invention. Such amino acid sequence variants preferably exhibit or inhibit a qualitative biological activity of a native TIE ligand homologue.

The term "fibrinogen domain" or "fibrinogen-like domain" is used to refer to amino acids from about position 278 to about position 498 in the known hTL-1 amino acid sequence; amino acids from about position 276 to about position 496 in the known hTL-2 amino acid sequence; amino acids from about position 180 to about 453 in the amino acid sequence of NL2; amino acids from about position 77 to about position 288 in the amino acid sequence of NL3; and amino acids from about position 238 to about position 460 in the amino acid sequence of FLS139, and to homologous domains in other TIE ligand homologues. The fibrinogen-like domain of NL2 is about 37–38% identical to that of the hTL-1 (TIE2L1) and hTL-2 (TIE2L2). The NL3 fibrinogen-like domain is about 37% identical to the fibrinogen-like domains of hTL-1 and hTL-2, while the FLS139 fibrinogen-like domain is about 32–33% identical to the fibrinogen-like domains of hTL-1 and hTL-2.

The term "nucleic acid molecule" includes RNA, DNA and cDNA molecules. It will be understood that, as a result of the degeneracy of the genetic code, a multitude of nucleotide sequences encoding a given TIE ligand may be produced. The present invention specifically contemplates every possible variation of nucleotide sequences, encoding the TIE ligand homologues of the present invention, based upon all possible codon choices. Although nucleic acid molecules which encode the TIE ligand homologues herein are preferably capable of hybridizing, under stringent conditions, to a naturally occurring TIE ligand homologue gene, it may be advantageous to produce nucleotide sequences encoding TIE ligand homologues, which possess a substantially different codon usage. For example, codons may be selected to increase the rate at which expression of the polypeptideoccurs in a particular prokaryotic or eukaryotic host cells, in accordance with the frequency with which a particular codon is utilized by the host. In addition, RNA transcripts with improved properties, e.g. half-life can be produced by proper choice of the nucleotide sequences encoding a given TIE ligand homologue.

"Sequence identity" shall be determined by aligning the two sequences to be compared following the Clustal method of multiple sequence alignment (Higgins et al., *Comput. Appl. Biosci.* 5, 151–153 (1989), and Higgins et al., Gene 73, 237–244 (1988)) that is incorporated in version 1.6 of the Lasergene biocomputing software (DNASTAR, Inc., Madison, Wis.), or any updated version or equivalent of this software.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology,* Wiley Interscience Publishers, (1995).

"Stringent conditions" or "high stringency conditions",as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as forrnamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual,* New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37–50° C. The skilled artisan will recognize how to adjust the temperature, ionic strength, etc. as necessaryto accommodate factors such as probe length and the like.

The term "epitope tagged" when used herein refers to a chimeric polypeptide comprising a TIE ligand homologue polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

The terms "biological activity" and "biologically active" with regard to a TIE ligand homologue of the present invention refer to the ability of a molecule to specifically bind to and signal through a native receptor of a TIE ligand, known or hereinafter discovered, (hereinafter referred to as a "TIE receptor"), e. g. a native TIE-2 receptor, or to block the ability of a native TIE receptor (e.g. TIE-2) to participate in signal transduction. Thus, the (native and variant) TIE ligands of the present invention include agonists and antagonists of a native TIE, e.g. TIE-2, receptor. Preferred biological activities of the TIE ligands of the present invention include the ability to induce or inhibit vascularization. The ability to induce vascularization will be useful for the treatment of biological conditions and diseases, where vascularization is desirable, such as wound healing, ischaemia, and diabetes. On the other hand, the ability to inhibit or block vascularization may, for example, be useful in preventing or attenuating tumor growth. Another preferred biological activity is the ability to affect muscle growth or development. A further preferred biological activity is the ability to influence bone development, maturation, or growth. Yet another preferred biological activity is the ability to inhibit endothelial cell growth and/or induce apoptosis.

The term "cytotoxic agent" as used herein refers to a substance that inhibits or prevents the function of cells and/or causes destruction of cells. The term is intended to include radioactive isotopes (e.g. $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeuticagent" is a chemical compound useful in the treatment of cancer. Examples of chemotherapeuticagents include adriamycin, doxorubicin, epirubicin, 5-fluorouracil, cytosine arabinoside ("Ara-C"), cyclophosphamide, thiotepa, busulfan, cytoxin, taxoids, e.g. paclitaxel (Taxol, Bristol-Myers Squibb Oncology, Princeton, N.J.), and doxetaxel (Taxotere, Rhône-Poulenc Rorer, Antony, Rnace), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, carminomycin, aminopterin, dactinomycin, mitomycins, esperamicins (see U.S. Pat. No. 4,675,187), melphalan and other related nitrogen mustards. Also included in this definition are hormonal agents that act to regulate or inhibit hormone action on tumors such as tamoxifen and onapristone.

A "growth inhibitory agent" when used herein refers to a compound or composition which inhibits growth of a cell, especially cancer cell overexpressing any of the genes identified herein, either in vitro or in vivo. Thus, the growth inhibitory agent is one which significantly reduces the percentage of cells overexpressing such genes in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxol, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogens, and antineoplastic drugs" by Murakami et al. (W B Saunders: Philadelphia, 1995), especially p. 13.

"Doxorubicin" is an athracycline antibiotic. The full chemical name of doxorubicin is (8S-cis)-10-[(3-amino-2, 3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

The term "cytokine" is a generic term for proteins released by one cell population which act on another cell as intercellular mediators. Examples of such cytokines are lymphokines, monokines, and traditional polypeptidehormones. Included among the cytokinesare growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-likegrowth factor-I and-II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

"Vascular endothelial growth factor"/ "vascularpermeability factor" (VEGF/VPF) is an endothelial cell-specific mitogen which has recently been shown to be stimulated by hypoxia and required for tumor angiogenesis (Senger et al., *Cancer* 46: 5629–5632 (1986); Kim et al., *Nature* 362:841–844 (1993); Schweiki et al., *Nature* 359: 843–845 (1992); Plate et al., *Nature* 359: 845–848 (1992)). It is a 34–43 kDa (with the predominant species at about 45 kDa) dimeric, disulfide-linked glycoprotein synthesized and secreted by a variety of tumor and normal cells. In addition, cultured human retinal cells such as pigment epithelial cells and pericytes have been demonstrated to secrete VEGF and to increase VEGF gene expression in response to hypoxia (Adamis et al., *Biochem. Biophys. Res. Commun.* 193: 631–638 (1993); Plouet et al., *Invest. Ophthalmol. Vis. Sci.* 34: 900 (1992); Adamis et al., *Invest. Ophthalmol. Vis. Sci.* 34: 1440 (1993); Aiello et al., *Invest. Opthalmol. Vis. Sci.* 35: 1868 (1994); Simorre-pinatel et al., *Invest. Opthalmol. Vis. Sci.* 35: 3393–3400(1994)). In contrast, VEGF in normal tissues is relatively low. Thus, VEGF appears to play a principle role in many pathological states and processes related to neovascularization. Regulation of VEGF expression in tissues affected by the various conditions described above could therefore be key in treatment or preventative therapies associated with hypoxia.

The term "agonist" is used to refer to peptide and non-peptide analogs of the native TIE ligand homologues of the present invention and to antibodies specifically binding such native TIE ligand homologues, provided that they have the ability to signal through a native TIE receptor (e.g. TIE-2). In other words, the term "agonist" is defined in the context of the biological role of the TIE receptor, and not in relation to the biological role of a native TIE ligand homologue, which, as noted before, may be an agonist or antagonist of the TIE receptor biological function. Preferred agonists possess the preferred biological activities of the TIE homologues as listed above, and include promoters of vascularization, molecules that play a role in bone formation maturation or growth, and promoters of muscle growth and/or development.

The term "antagonist" is used to refer to peptide and non-peptide analogs of the native TIE ligand homologues of the present invention and to antibodies specifically binding such native TIE ligand homologues, provided that they have the ability to inhibit the biological function of a native TIE receptor (e.g. TIE-2). Again, the term "antagonist" is defined in the context of the biological role of the TIE receptor, and not in relation to the biological activity of a native TIE ligand homologue, which may be either an agonist or an antagonist of the TIE receptor biological function. Preferred antagonists are inhibitors of vasculogenesis, or pathological bone or muscle development or growth.

"Tumor", as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colorectal cancer, endometrial carcinoma, salivary gland carcinoma, kidney cancer, liver cancer, vulval cancer, thyroid cancer, hepatic carcinoma and various types of head and neck cancer.

"Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. In tumor (e.g. cancer) treatment, a therapeutic agent may directly decrease the pathology of tumor cells, or render the tumor cells more susceptible to treatment by other therapeutic agents, e.g. radiation and/or chemotherapy.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, etc.

"Mammal" for purposes of treatment refers to any animal classified as a mammal, including humans, domestic and farm animals, and zoo, sports, or pet animals, such as dogs, horses, cats, cows, etc. Preferably, the mammal is human.

Administration "in combination with" one or more further therapeutic agents includes simultaneous (concurrent) and consecutive administration in any order.

The term "functional derivative" is used to define biologicallyactive amino acid sequence variants of the native TIE ligand homologues of the present invention, as well as covalent modifications, including derivatives obtained by reaction with organic derivatizing agents, post-translational modifications; derivatives with nonproteinaceous polymers, and immunoadhesins.

The term "isolated" when used to describe the various polypeptides described herein, means polypeptides that have been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficiento obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinantcells, since at least one component of the TIE ligand's natural environment will not be present. Ordinarily, however, isolated polypeptide will be prepared by at least one purification step.

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes nucleic acid molecules contained in cells that ordinarily express an TIE ligand of the present invention, where, for example, the nucleic acid molecule is in a chromosomal location different from that of natural cells.

The term "amino acid sequence variant" refers to molecules with some differences in their amino acid sequences as compared to a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule. Deletional variants include those having C- and/or N-terminal deletions (truncations) as well as variants with internal deletions of one or more amino acids. The preferred deletional variants of the present invention contain deletions outside the fibrinogen-like domain of a native TIE ligand homologue of the present invention.

The amino acid sequence variants of the present invention may contain various combinations of amino acid substitutions, insertions and/or deletions, to produce molecules with optimal characteristics.

The amino acids may be classified according to the chemical composition and properties of their side chains. They are broadly classified into two groups, charged and uncharged. Each of these groups is divided into subgroups to classify the amino acids more accurately.

1. Charged Amino Acids

Acidic Residues: aspartic acid, glutamic acid

Basic Residues: lysine, arginine, histidine

II. Uncharged Amino Acids

Hydrophilic Residues: serine, threonine, asparagine, glutamine

Aliphatic Residues: glycine, alanine, valine, leucine, isoleucine

Non-polar Residues: cysteine, methionine, proline

Aromatic Residues: phenylalanine, tyrosine, tryptophan

Conservative substitutions involve exchanging a member within one group for another member within the same group, whereas non-conservative substitutions will entail exchanging a member of one of these classes for another. Variants obtained by non-conservative substitutions are expected to result in significant changes in the biological properties/function of the obtained variant Amino acid sequence deletions generally range from about 1 to 30 residues, more preferably about 1 to 10 residues, and typically are contiguous. Deletions may be introduced into regions not directly involved in the interaction with a native TIE receptor. Deletions are preferably performed outside the fibrinogen-like regions at the C-terminus of the TIE ligand homologues of the present invention.

Amino acid insertions include amino- and/or carboxyl-terminal fusions ranging in length from one residue to polypeptides containing a hundred or more residues, as well as intrasequence insertions of single or multiple amino acid residues. Intrasequence insertions (i.e. insertions within the TIE ligand homologue amino acid sequence) may range generally from about 1 to 10 residues, more preferably 1 to 5 residues, more preferably 1 to 3 residues. Examples of terminal insertions include the TIE ligand homologues with an N-terminal methionyl residue, an artifact of its direct expression in bacterial recombinantcell culture, and fusion of a heterologous N-terminal signal sequence to the N-terminus of the TIE ligand homologue molecule to facilitate the secretion of the mature TIE ligand homologue from recombinant host cells. Such signal sequences will generally be obtained from, and thus homologous to, the intended host cell species. Suitable sequences include, for example, STII or Ipp for *E. coli,* alpha factor for yeast, and viral signals such as herpes gD for mammalian cells.

Other insertional variants of the native TIE ligand molecules include the fusion of the N- or C-terminus of the TIE ligand homologue molecule to immunogenic polypeptides, e.g. bacterial polypeptides such as beta-lactamase or an enzyme encoded by the *E. coli* trp locus, or yeast protein, and C-terminal fusions with proteins having a long half-life such as immunoglobulin regions (preferably immunoglobulin constant regions), albumin, or ferritin, as described in WO 89/02922 published on Apr. 6, 1989.

Since it is often difficult to predict in advance the characteristic sofa variant TIE ligand homologue, it will be appreciated that some screening will be needed to select the optimum variant.

Amino acid sequence variants of native TIE ligand homologues of the present invention are prepared by methods known in the art by introducing appropriate nucleotide changes into a native or variant TIE ligand homologue DNA, or by in vitro synthesis of the desired polypeptide. There are two principal variables in the construction of amino acid sequence variants: the location of the mutation site and the nature of the mutation. With the exception of naturally-occurring alleles, which do not require the manipulation of the DNA sequence encoding the TIE ligand homologue, the amino acid sequence variants of the TIE ligand homologues are preferably constructed by mutating the DNA, either to arrive at an allele or an amino acid sequence variant that does not occur in nature.

One group of the mutations will be created within the domain or domains of the TIE ligand homologues of the present invention identified as being involved in the interaction with a TIE receptor, e.g. TIE-1 or TIE-2, or a receptor yet to be discovered.

Alternatively or in addition, amino acid alterations can be made at sites that differ in TIE ligand homologues from various species, or in highly conserved regions, depending on the goal to be achieved.

Sites at such locations will typically be modified in series, e.g. by (1) substituting first with conservative choices and then with more radical selections depending upon the results achieved, (2) deleting the target residue or residues, or (3) inserting residues of the same or different class adjacent to the located site, or combinations of options 1–3.

One helpful technique is called "alanine scanning" (Cunningham and Wells, Science 244, 1081–1085 [1989]). Here, a residue or group of target residues is identified and substituted by alanine or polyalanine. Those domains demonstrating functional sensitivity to the alanine substitutions are then refined by introducing further or other substituents at or for the sites of alanine substitution.

After identifying the desired mutation(s), the gene encoding an amino acid sequence variant of a TIE ligand homologue can, for example, be obtained by chemical synthesis as hereinabove described.

More preferably, DNA encoding a TIE ligand homologue amino acid sequence variant is prepared by site-directed mutagenesis of DNA that encodes an earlier prepared variant or a nonvariant version of the ligand. Site-directed(site-specific)mutagenesis allows the production of ligand variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the techniques of site-specific mutagenesis are well known in the art, as exemplified by publications such as, Edelman et al., *DNA* 2, 183 (1983). As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, A. Walton, ed., Elsevier, Amsterdam (1981). This and other phage vectors are commercially available and their use is well known to those skilled in the art. A versatile and efficient procedure for the construction of oligodeoxyribonucleotide directed site-specific mutations in DNA fragments using M13-derived vectors was published by Zoller, M. J. and Smith, M., *Nucleic Acids Res.* 10, 6487–6500 [1982]). Also, plasmid vectors that contain a single-stranded phage origin of replication (Veira et al., *Meth. Enzymol.* 153 3 [1987]) may be employed to obtain single-stranded DNA. Alternatively, nucleotide substitutions are introduced by synthesizing the appropriate DNA fragment in vitro, and amplifying it by PCR procedures known in the art.

In general, site-specific mutagenesis herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci. USA* 75, 5765 (1978). This primer is then annealed with the single-stranded protein sequence-containing vector, and subjected to DNA-polymerizing enzymes such as, *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate host cells such as JP101 cells, and clones are selected that include recombinant vectors bearing the mutated sequence arrangement. Thereafter, the mutated region may be removed and placed in an appropriate expression vector for protein production.

The PCR technique may also be used in creating amino acid sequence variants of a TIE ligand. When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer or performing a second PCR with different mutant primers and ligating the two resulting PCR fragments simultaneously to the vector fragment in a three (or more) part ligation.

In a specific example of PCR mutagenesis, template plasmid DNA (1 $\mu$g) is linearized by digestion with a restriction endonuclease that has a unique recognition site in the plasmid DNA outside of the region to be amplified. Of this material, 100 ng is added to a PCR mixture containing PCR buffer, which contains the four deoxynucleotidetriphosphates and is included in the GeneAmp® kits (obtained from Perkin-Elmer Cetus, Norwalk, Conn. and Emeryville, Calif.), and 25 pmole of each oligonucleotide primer, to a final volume of 50 µl. The reaction mixture is over layered with 35 µl mineral oil. The reaction is denatured for 5 minutes at 100° C., placed briefly on ice, and then 1 µl *Thermus aquaticus* (Taq) DNA polymerase (5 units/l), purchased from Perkin-ElmerCetus, Norwalk, Conn. and Emeryville, Calif.) is added below the mineral oil layer. The reaction mixture is then inserted into a DNA Thermal Cycler (purchased from Perkin-Elmer Cetus) programmed as follows:

2 min. 55° C., 30 sec. 72° C., then 19 cycles of the following:

30 sec. 94° C., 30 sec. 55° C., and 30 sec. 72° C.

At the end of the program, the reaction vial is removed from the thermal cycler and the aqueous phase transferred to a new vial, extracted with phenol/chloroform (50:50 vol), and ethanol precipitated, and the DNA is recovered by standard procedures. This material is subsequently subjected to appropriate treatments for insertion into a vector.

Another method for preparing variants, cassette mutagenesis, is based on the technique described by Wells et al. [*Gene* 34, 315 (1985)]. The starting material is the plasmid (or vector) comprising the TIE ligand homologue DNA to be mutated. The codon(s) within the TIE ligand homologue to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the DNA encoding the TIE ligand homologue. After the restriction sites have been introduced into the plasmid, the plasmid is cut at these sites to linearize it. A double-stranded oligonucleotide encoding the sequence of the DNA between the restriction site but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated TIE ligand homologue DNA sequence.

Additionally, the so-called phagemid display method may be useful in making amino acid sequence variants of native or variant TIE ligand homologues. This method involves (a) constructing a replicable expression vector comprising a first gene encoding an receptor to be mutated, a second gene encoding at least a portion of a natural or wild-type phage coat protein wherein the first and second genes are heterologous, and a transcription regulatory element operably linked to the first and second genes, thereby forming a gene fusion encoding a fusion protein; (b) mutating the vector at one or more selected positions within the first gene thereby forming a family of related plasmids; (c) transforming suitable host cells with the plasmids; (d) infecting the transformed host cells with a helper phage having a gene encoding the phage coat protein; (e) culturing the transformed infected host cells under conditions suitable for forming recombinant phagemid particles containing at least a portion of the plasmid and capable of transforming the host, the conditions adjusted so that no more than a minor amount of phagemid particles display more than one copy of the fusion protein on the surface of the particle; (f) contacting the phagemid particles with a suitable antigen so that at least a portion of the phagemid particles bind to the antigen; and (g) separating the phagemid particles that bind from those that do not. Steps (d) through (g) can be repeated one or more times. Preferably in this method the plasmid is under tight control of the transcription regulatory element, and the culturing conditions are adjusted so that the amount or number of phagemid particles displaying more than one copy of the fusion protein on the surface of the particle is less than about 1%. Also, preferably, the amount of phagemid particles displaying more than one copy of the fusion protein is less than 10% of the amount of phagemid particles displaying a single copy of the fusion protein. Most preferably, the amount is less than 20%. Typically in this method, the expression vector will further contain a secretory signal sequence fused to the DNA encoding each subunit of the polypeptide and the transcription regulatory element will be a promoter system. Preferred promoter systems are selected from lac Z, $\lambda_{PL}$, tac, T7 polymerase, tryptophan, and alkaline phosphatasepromoters and combinations thereof. Also, normally the method will employ a helper phage selected from M13K07, M13R408, M13-VCS, and Phi X 174. The preferred helper phage is M13K07, and the preferred coat protein is the M13 Phage gene III coat protein. The preferred host is *E. coli,* and protease-deficient strains of *E. coli.*

Further details of the foregoing and similar mutagenesis techniques are found in general textbooks, such as, for example, Sambrook et al., *Molecular Cloning: A laboratory Manual* (New York: Cold Spring Harbor Laboratory Press, 1989), and *Current Protocols in Molecular Biology,* Ausubel et al., eds., Wiley-Interscience, 1991.

"Immunoadhesins" are chimeras which are traditionally constructed from a receptor sequence linked to an appropriate immunoglobulin constant domain sequence (immunoadhesins). Such structures are well known in the art. Immunoadhesins reported in the literature include fusions of the T cell receptor* [Gascoigne et al., *Proc. Natl. Acad. Sci. USA* 84, 2936–2940 (1987)]; CD4* [Capon et al., *Nature* 337, 525–531 (1989); Traunecker et al., *Nature* 339, 68–70 (1989); Zettmeissl et al., *DNA Cell Biol. USA* 9, 347–353 (1990); Byrn et al., *Nature* 344, 667–670 (1990)]; L-selectin (homing receptor) [Watson et al., *J. Cell. Biol.* 110, 2221–2229 (1990); Watson et al., *Nature* 349, 164–167 (1991)]; CD44* [Aruffo et al., *Cell* 61, 1303–1313 (1990)]; CD28* and B7* [Linsley et al., J. Exp. Med. 173, 721–730 (1991)]; CTLA-4* [Lisley et al.,*J. Exp. Med.* 174, 561–569 (1991)]; CD22* [Stamenkovic et al., *Cell* 66. 1133–1144 (1991)]; TNF receptor [Ashkenazi et al., *Proc. Natl. Acad. Sci. USA* 88, 10535–10539 (1991); Lesslauer et al., *Eur. J. Immunol.* 27, 2883–2886 (1991); Peppel et al., *J. Exp. Med.* 174, 1483–1489 (1991)]; NP receptors [Bennett et al., J. Biol. Chem. 266, 23060–23067 (1991)]; IgE receptor α-chain* [Ridgway and Gorman, *J. Cell. Biol.* 115, abstr. 1448 (1991)]; HGF receptor [Mark, M. R. et al., 1992, J. Biol. Chem. submitted], where the asterisk (*) indicates that the receptor is member of the immunoglobulin superfamily.

Ligand-immunoglobulinchimeras are also known, and are disclosed, for example, in U.S. Pat. No. 5,304,640 (for L-selectin ligands); U.S. Pat. Nos. 5,316,921 and 5,328,837 (for HGF variants). These chimeras can be made in a similar way to the construction of receptor-immunoglobulin chimeras.

Covalent modifications of the TIE ligand homologues of the present invention are included within the scope herein. Such modifications are traditionally introduced by reacting targeted amino acid residues of the TIE ligand with an organic derivatizing agent that is capable of reacting with selected sides or terminal residues, or by harnessing mechanisms of post-translational modifications that function in selected recombinant host cells. The resultant covalent derivatives are useful in programs directed at identifying residues important for biological activity, for immunoassays, or for the preparation of anti-TIE ligand antibodies for immunoaffinity purification of the recombinant. For example, complete inactivation of the biological activity of the protein after reaction with ninhydrin would suggest that at least one arginyl or lysyl residue is critical for its activity, whereafter the individual residues which were modified under the conditions selected are identified by isolation of a peptide fragment containing the modified amino acid residue. Such modifications are within the ordinary skill in the art and are performed without undue experimentation.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Parabromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high PKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay.

Carboxyl side groups (aspartyl or glutamyl) are selectively modified by reaction with carbodiimides (R'—N=C=N—R') such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl, threonyl or tyrosyl residues, methylation of the α-amino groups of lysine, arginine, and histidine side chains (T. E. Creighton, *Proteins: Structure and Molecular Properties*, W. H. Freeman & Co., San Francisco, pp. 79–86 [1983]), acetylation of the N-terminal amine, and amidation of any C-terminal carboxyl group. The molecules may further be covalently linked to nonproteinaceous polymers, e.g. polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337.

Derivatization with bifunctional agents is useful for preparing intramolecular aggregates of the TIE ligand with polypeptides as well as for cross-linking the TIE ligand polypeptide to a water insoluble support matrix or surface for use in assays or affinity purification. In addition, a study of interchain cross-links will provide direct information on conformational structure. Commonly used cross-linking agents include 1,1-bis(diazoacetyl)-2-phenylethane, glutaraldehyde, N-hydroxysuccinimide esters, homobifunctional imidoesters, and bifunctional maleimides. Derivatizing agents such as methyl-3-[(p-azidophenyl)dithio] propioimidate yield photo activatable intermediates which are capable of forming cross-links in the presence of light. Alternatively, reactive water insoluble matrices such as cyanogen bromide activated carbohydrates and the systems reactive substrates described in U.S. Pat. Nos. 3,959,642; 3,969,287; 3,691,016; 4,195,128; 4,247,642; 4,229,537; 4,055,635; and 4,330,440 are employed for protein immobilization and cross-linking.

Certain post-translational modifications are the result of the action of recombinant host cells on the expressed polypeptide. Glutaminyl and aspariginyl residues are frequently post-translationally deamidated to the corresponding glutamyl and aspartyl residues. Alternatively, these residues are deamidated under mildly acidic conditions. Either form of these residues falls within the scope of this invention.

Other post-translational modifications include hydroxylation of proline and lysine, phosphorylation of hydroxyl groups of seryl, threonyl or tyrosyl residues, methylation of the α-amino groups of lysine, arginine, and histidine side chains [T. E. Creighton, *Proteins: Structure and Molecular Properties*, W. H. Freeman & Co., San Francisco, pp. 79–86 (1983)].

Other derivatives comprise the novel peptides of this invention covalently bonded to a nonproteinaceous polymer. The nonproteinaceous polymer ordinarily is a hydrophilic synthetic polymer, i.e. a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyvinylalkylene ethers such a polyethylene glycol, polypropylene glycol.

The TIE ligand homologues may be linked to various nonproteinaceous polymers, such as polyethylene glycol (PEG), polypropylene glycol or polyoxyalkylenes, in the mannerset forth in U.S. Pat. Nos. 4,640,835; 4,496,689; 4,301,144; 4,670,417; 4,791,192 or 4,179,337. These variants, just as the immunoadhesins of the present invention are expected to have longer half-lives than the corresponding native TIE ligand homologues.

The TIE ligand homologues may be entrapped in microcapsules prepared, for example, by coacervation techniques or by interfacial polymerization, in colloidal drug delivery systems (e.g. liposomes, albumin microspheres, microemulsions, nano-particles and nanocapsules), or in macroemulsions. Such techniques are disclosed in *Remingiton's Pharmaceutical Sciences,* 16th Edition, Osol, A., Ed. (1980).

The term "native TIE receptor" is used herein to refer to a TIE receptor of any animal species, including, but not limited to, humans, other higher primates, e.g. monkeys, and rodents, e.g. rats and mice, known or hereinafter discovered. The definition specifically includes the TIE-2 receptor, disclosed, for example, in PCT Application Ser. No. WO 95/13387 (published May 18, 1995), and the endothelial cell receptor tyrosine kinase termed "TIE" in PCT Application Publication No. WO 93/14124 (published Jul. 22 1993), and preferably is TIE-2.

B. Anti-TIE Ligand Homologue Antibodies

The present invention covers agonist and antagonist antibodies, specifically binding the TIE ligand homologues. The antibodies may be monoclonal or polyclonal, and include, without limitation, mature antibodies, antibody fragments (e.g. Fab, F(ab')$_2$, F$_v$, etc.), single-chain antibodies and various chain combinations.

The term "antibody" is used in the broadest sense and specifically covers single monoclonal antibodies (including agonist, antagonist, and neutralizing antibodies) specifically binding a TIE ligand of the present invention and antibody compositions with polyepitopic specificity.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include hybrid and recombinant antibodies produced by splicing a variable (including hypervariable) domain of an anti-TIE ligand homologue antibody with a constant .domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and F$_v$), so long as they exhibit the desired biological activity. See, eg. U.S. Pat. No. 4,816,567 and Mage et al., in *Monoclonal Antibody Production Techniques and Applications,* pp. 79–97 (Marcel Dekker, Inc.: New York, 1987).

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, *Nature,* 256:495 (1975), or may be made by recombinant DNA methods such as described in U.S. Pat. No. 4,816,567. The "monoclonal antibodies" may also be isolated from phage libraries generated using the techniques described in McCafferty et al., *Nature,* 348:552–554 (1990), for example.

"Humanized" forms of non-human (e.g. murine) antibodies are specific chimeric imnunoglobulins, immunoglobulin chains, or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody)in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin.

Polyclonal antibodies to a TIE ligand homologue of the present invention generally are raised in animals by multiple subcutaneous (sc) or intraperitoneal (ip) injections of the TIE ligand and an adjuvant. It may be useful to conjugate the TIE ligand or a fragment containing the target amino acid sequence to a protein that is immunogenic in the species to be immunized, e.g. keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glytaraldehyde, succinic anhydride, $SOCl_2$, or $R^1N$=C=NR, where R and $R^1$ are different alkyl groups.

Animals are immunized against the immunogenic conjugates or derivatives by combining 1 mg or 1 μg of conjugate (for rabbits or mice, respectively) with 3 volumes of Freud's complete adjuvant and injecting the solution intradermally at multiple sites. One month later the animals are boosted with ⅕ to ⅒ the original amount of conjugate in Freud's complete adjuvant by subcutaneous injection at multiple sites. 7 to 14 days later the animals are bled and the serum is assayed for anti-TIE ligand antibody titer. Animals are boosted until the titer plateaus. Preferably, the animal boosted with the conjugate of the same TIE ligand, but conjugated to a different protein and/or through a different cross-linking reagent. Conjugates also can be made in recombinant cell culture as protein fusions. Also, aggregating agents such as alum are used to enhance the immune response.

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies.

For example, the anti-TIE ligand homologue monoclonal antibodies of the invention may be made using the hybridoma method first describedby Kohler & Milstein, Nature 256:495 (1975), or may be made by recombinant DNA methods [Cabilly, et al., U.S. Pat. No. 4,816,567].

In the hybridoma method, a mouse or other appropriate host animal, such as hamster is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell [Goding, *Monoclonal Antibodies: Principles and Practice*, pp.59–103 (Academic Press, 1986)].

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin,and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies [Kozbor, J. Immunol. 133:3001 (1984); Brodeur, et al., *Monoclonal Antibody Production Techniques and Applications*, pp.51–63 (Marcel Dekker, Inc., New York, 1987)].

Culture medium in which hybridoma cells are growing is assayed for production of monoclonal antibodies directed against the TIE ligand homologue. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson & Pollard, Anal. Biochem. 107:220 (1980).

After hybridoma cells are identified that produce antibodies of the desired specificity, affinity, and/or activity, the clones may be subcloned by limiting dilution procedures and grown by standard methods. Goding, *Monoclonal Antibodies: Principles and Practice*, pp.59–104 (Academic Press, 1986). Suitable culture media for this purpose include, for example, Dulbecco's Modified Eagle's Medium or RPMI-1640 medium. In addition, the bybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, et al., *Proc. Nat. Acad. Sci.* 81, 6851 (1984), or by covalently joining to the immunoglobulin coding sequence all or part of the coding sequence for a non-immunoglobulinpolypeptide.

In that manner, "chimeric" or "hybrid" antibodies are prepared that have the binding specificity of an anti-TIE ligand monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for a TIE ligand of the present invention and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; biotin; radioactive isotopic labels, such as, e.g., $^{125}I$, $^{32}P$, $^{14}C$, or $^3H$, or an enzyme, such as alkaline phosphatase, beta-galactosidase or horseradish peroxidase.

Any method known in the art for separately conjugating the antibody to the detectable moiety may be employed, including those methods described by Hunter, et al., *Nature* 144:945 (1962); David, et al., *Biochemistry* 13:1014 (1974); Pain, et al., *J. Immunol. Meth.* 40:219 (1981); and Nygren, *J. Histochem. and Cytochem.* 30:407 (1982).

The antibodies of the present invention may be employed in any known assay method, such as competitive binding assays, direct and indirect sandwich assays, and immunoprecipitation assays. Zola, *Monoclonal Antibodies: A Manual of Techniques*, pp.147–158 (CRC Press, Inc., 1987).

Competitive binding assays rely on the ability of a labeled standard (which may be a TIE ligand homologue or an immunologically reactive portion thereof) to compete with the test sample analyte (TIE ligand) for binding with a limited amount of antibody. The amount of TIE ligand homologue in the test sample is inversely proportional to the amount of standard that becomes bound to the antibodies. To facilitate determining the amount of standard that becomes bound, the antibodiesgenerally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibodywhich is immobilizedon a solid support, and thereaftera second antibody binds to the analyte, thus formingan insolublethree part complex. David & Greene, U.S. Pat. No. 4,376,110. The second antibody may itselfbe labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers[Jones et al., Nature 321, 522–525 (1986); Riechmann et al., Nature 332,323–327 (1988Verhoeyen et al., Science 239 1534–1536 (1988)], by substituting rodent CDRs or CDR sequences for the corresponding sequences of a human antibody. Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is importantthat antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobul in models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

Alternatively, it is now possible to produce transgenic animals (e.g. mice) that are capable, upon immunization, of producing a full repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulingene array in such germ-line mutant mice will result in the production of human antibodies upon antigen challenge. See, e.g. Jakobovits et al., Proc. Natl. Acad. Sci. USA 90, 2551–255 (1993); Jakobovits et al., Nature 362, 255–258 (1993).

Bispecific antibodies are monoclonal,preferably human or humanized, antibodies that have binding specificities for at least two different antigens. In the present case, one of the binding specificities is for a particular TIE ligand, the other one is for any other antigen, and preferably for another ligand. For example, bispecific antibodies specifically binding two different TIE ligand homologues are within the scope of the present invention.

Methods for making bispecific antibodies are known in the art.

Traditionally, the recombinant production of bispecific antibodies is based on the coexpression of two immunoglobulin heavy chain-light chain pairs, where the two heavy chains have different specificities (Millstein and Cuello, Nature 305, 537–539 (1983)). Because of the random assortment of immunoglobulin-heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829 (published May 13, 1993), and in Traunecker et al., EMBO 10, 3655–3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, and second and third constant regions of an immunoglobulin heavy chain (CH2 and CH3). It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodimentofthis approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation.

For further details of generating bispecific antibodies see, for example, Suresh et al., Methods in Enzymology 121, 210 (1986).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/1116 1; and Hollinger et al., Proc. Natl. Acad. Sci. USA, 90:6444–6448 (1993).

An "isolated" antibody is defined similarly to the definition provided hereinabove for isolated polypeptides. Specifically, an "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatographycolumn). This term also includes a discontinuous solid phase of discrete particles, such as those described in U.S. Pat. No. 4,275,149.

A "liposome" is a small vesicle composed of various types of lipids, phospholipidsand/or surfactant which is useful for delivery of a drug (such as the anti-ErbB2 antibodies disclosed herein and, optionally, a chemotherapeutic agent) to a mammal. The components of the liposome are commonly arranged in a bilayer formation, similar to the lipid arrangement of biological membranes.

Antibody "agonists" and "antagonists" are as hereinabove defined.

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies,* vol. 113, Rosenburg and Moore eds., Springer-Verlag, N.Y., pp. 269–315 (1994).

C. CLONING AND EXPRESSION OF THE TIE LIGAND HOMOLOGUES

In the context of the present invention the expressions "cell", "cell line", and "cell culture" are used interchangeably, and all such designations include progeny. It is also understood that all progeny may not be precisely identical in DNA content, due to deliberate or inadvertent mutations. Mutant progeny that have the same function or biological property, as screened for in the originally transformed cell, are included.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

Expression and cloning vectors are well known in the art and contain a nucleic acid sequence that enables the vector to replicate in one or more selected host cells. The selection of the appropriate vector will depend on 1) whether it is to be used for DNA amplification or for DNA expression,2) the size of the DNA to be inserted into the vector, and 3) the host cell to be transformed with the vector. Each vector contains various components depending on its function (amplification of DNA of expression of DNA) and the host cell for which it is compatible. The vector components generally include, but are not limited to, one or more of the following: a signal sequence, an origin of replication, one or more marker genes, an enhancer element, a promoter, and a transcription termination sequence.

(i) Signal Sequence Component

In general, the signal sequence may be a component of the vector, or it may be a part of the TIE ligand molecule that is inserted into the vector. If the signal sequence is heterologous, it should be selected such that it is recognized and processed (i.e. cleaved by a signal peptidase) by the host cell.

Heterologous signal sequences suitable for prokaryotic host cells are preferably prokaryotic signal sequences, such as the α-amylase, ompA, ompC, ompE, ompF, alkaline phosphatase, penicillinase, Ipp, or heat-stable enterotoxin II leaders. For yeast secretion the yeast invertase, amylase, alpha factor, or acid phosphatase leaders may, for example, be used. In mammalian cell expression mammalian signal sequences are most suitable. The listed signal sequences are for illustration only, and do not limit the scope of the present invention in any way.

(ii) Origin of Replication Component

Both expression and cloning vectors contain a nucleic acid sequence that enabled the vector to replicate in one or more selected host cells. Generally, in cloning vectors this sequence is one that enables the vector to replicate independently of the host chromosomes, and includes origins of replication or autonomously replicating sequences. Such sequence are well known for a variety of bacteria, yeast and viruses. The origin of replication from the well-known plasmid pBR322 is suitable for most gram negative bacteria, the $2\mu$ plasmid origin for yeast and various viral origins (SV40, polyoma, adenovirus, VSV or BPV) are useful for cloning vectors in mammalian cells. Origins of replication are not needed for mammalian expression vectors (the SV40 origin may typically be used only because it contains the early promoter). Most expression vectors are "shuttle" vectors, i.e. they are capable of replication in at least one class of organisms but can be transfected into another organism for expression. For example, a vector is cloned in E. coli and then the same vector is transfected into yeast or mammalian cells for expression even though it is not capable of replicating independently of the host cell chromosome.

DNA is also cloned by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of the DNA encoding the desired heterologous polypeptide. However, the recovery of genomic DNA is more complex than that of an exogenously replicated vector because restriction enzyme digestion is required to excise the encoded polypeptide molecule.

(iii) Selection Gene Component

Expression and cloning vectors should contain a selection gene, also termed a selectable marker.

This is a gene that encodes a protein necessary for the survival or growth of a host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, e.g. ampicillin, neomycin, methotrexate or tetracycline, (b) complementauxotrophic deficiencies, or (c) supply critical nutrients not available from complex media, e.g. the gene encoding D-alanine racemase for bacilli.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin [Southern et al., J. Molec. Appl. Genet. 1, 327 (1982)], mycophenolic acid [Mulligan et al., Science 209, 1422 (1980)], or hygromycin [Sudgen et al., Mol. Cel. Biol. 5, 410–413 (1985)]. The three examples given above employ bacterial genes under eukaryotic control to convey resistance to the appropriate drug G418 or neomycin (geneticin), xgpt (mycophenolic acid), or hygrom ycin, respectively.

Other examples of suitable selectable markers for mammalian cells are dihydrofolate reductase (DHFR) or thymidine kinase. Such markers enable the identification of cells which were competent to take up the desired nucleic acid. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the desired polypeptide. Amplification is the process by which genes in greater demand for the production of a protein critical for growth are reiterated in tandem within the chromosomes of successive generations of recombinant cells. Increased quantities of the desired polypeptide are synthesized from the amplified DNA.

For example, cells transformed with the DHFR selection gene are first identified by culturing all of the transformants in a culture medium which lacks hypoxanthine, glycine, and thymidine. An appropriate host cell in this case is the Chinese hamster ovary (CHO) cell line deficient in DHFR activity, prepared and propagated as described by Urlaub and Chasin, Proc. Nat'l. Acad. Sci. USA 77, 4216 (1980). A particularly usefull DHFR is a mutant DHFR that is highly resistant to MTX (EP 117,060). This selection agent can be used with any otherwise suitable host, e.g. ATCC No. CCL61 CHO-K1, notwithstanding the presence of endogenous DHFR. The DNA encoding DHFR and the desired polypeptide, respectively, then is amplified by exposure to an agent (methotrexate, or MTX) that inactivates the DHFR. One ensures that the cell requires more DHFR (and consequently amplifies all exogenous DNA) by selecting only for cells that can grow in successive rounds of ever-greater MTX concentration. Alternatively, hosts co-transformed with genes encoding the desired polypeptide, wild-type DHFR, and another selectable marker such as the neo gene can be identified using a selection agent for the selectable marker such as G418 and then selected and amplified using methotrexate in a wild-type host that contains endogenous DHFR. (See also U.S. Pat. No. 4,965,199).

A suitable selection gene for use in yeast is the trp1 gene present in the yeast plasmid YRp7 (Stinchcomb et al., 1979, Nature 282:39; Kingsman et al., 1979, Gene 7:141; or Tschemper et al., 1980, Gene 10:157). The Trp1 gene provides a selection marker for a mutant strain of yeast lacking the ability to grow in tryptophan, for example, ATCC No. 44076 or PEP4-1 (Jones, 1977, Genetics 85:12). The presence of the trp1 lesion in the yeast host cell genome then provides an effective environment for detecting transformation by growth in the absence of tryptophan. Similarly, Leu2 deficient yeast strains (ATCC 20,622 or 38,626) are complemented by known plasmids bearing the Leu2 gene.

(iv) Promoter Component

Expression vectors, unlike cloning vectors, should contain a promoter which is recognized by the host organism and is operably linked to the nucleic acid encoding the desired polypeptide. Promoters are untranslated sequences located upstream from the start codon of a structural gene (generally within about 100 to 1000 bp) that control the transcription and translation of nucleic acid under their control. They typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters are operably linked to DNA encoding the desired polypeptide by removing them from their gene of origin by restriction enzyme digestion, followed by insertion 5' to the start codon for the polypeptide to be expressed. This is not to say that the genomic promoter for a TIE ligand is not usable. However, heterologous promoters generally will result in greater transcription and higher yields of expressed TIE ligand homologues as compared to the native TIE ligand promoters.

Promoters suitable for use with prokaryotic hosts include the P-lactamase and lactose promoter systems (Chang et al., Nature 275:615 (1978); and Goeddel et al., Nature 281:544 (1979)), alkaline phosphatase, a tryptophan (trp) promoter system (Goeddel, Nucleic Acids Res. 8:4057 (1980) and EPO Appln. Publ. No. 36,776)and hybrid promoters such as the tac promoter (H. de Boer et al., Proc. Nat'l. Acad. Sci. USA 80:21–25 (1983)). However, other known bacterial promoters are suitable. Their nucleotide sequences have been published, thereby enabling a skilled worker operably to ligate them to DNA encoding a TIE ligand (Siebenlist et al., Cell 20:269 (1980)) using linkers or adaptors to supply any required restriction sites. Promoters for use in bacterial systems also will contain a Shine-Dalgarno (S.D.) sequence operably linked to the DNA encoding a TIE ligand.

Suitable promoting sequences for use with yeast hosts include the promoters for 3-phosphoglycerate kinase (Hitzeman et al. *J. Biol. Chem.* 25:2073 (1980)) or other glycolytic enzymes (Hess et al., *J. Adv. Enzyme Reg.* 7:149 (1978); and Holland, *Biochemistry* 17:4900 (1978)), such as enolase, glyceraldehyde-3-phospate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R.

Hitzeman et al., EP 73,657A. Yeast enhancers also are advantageously used with yeast promoters.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into mammalian expression vectors.

TIE ligand transcription from vectors in mammalian host cells may be controlled by promoters obtained from the genomes of viruses such as polyoma virus, fowlpox virus (UK 2,211,504published Jul. 5, 1989), adenovirus (such as Adenovirus 2), bovine papilloma virus, avian sarcoma virus, cytomegalovirus, aretrovirus, hepatitis-B virus and most preferably Simian Virus 40 (SV40), from heterologous mammalian promoters, e.g. the actin promoter or an immunoglobulin promoter, from heat shock promoters, and from the promoter normally associated with the TIE ligand sequence, provided such promoters are compatible with the host cell systems.

The early and late promoters of the SV40 virus are conveniently obtained as an SV40 restriction fragment which also contains the SV40 viral origin of replication [Fiers et al., *Nature* 273:113 (1978), Mulligan and Berg, *Science* 209, 1422–1427 (1980); Pavlakis et al., *Proc. Natl. Acad. Sci. USA* 78, 7398–7402 (1981)]. The immediate early promoter of the human cytomegalovirus is conveniently obtained as a HindIII E restriction fragment [Greenaway et al., *Gene* 18, 355–360(1982)]. A system for expressing DNA in mammalian hosts using the bovine papilloma virus as a vector is disclosed in U.S. Pat. No. 4,419,446. A modification of this system is described in U.S. Pat. No. 4,601,978. See also, Gray et al., *Nature* 295, 503–508 (1982) on expressing cDNA encoding human immune interferon in monkey cells; Reyes et al., *Nature* 297, 598–601 (1982) on expressing human β-interferon cDNA in mouse cells under the control of a thymidine kinase promoterfrom herpes simplex virus; Canaani and Berg, *Proc. Natl. Acad. Sci. USA* 79, 5166–5170 (1982) on expression of the human interferon β1 gene in cultured mouse and rabbit cells; and Gorman et al., *Proc. Natl. Acad. Sci. USA* 79, 6777–6781 (1982) on expression of bacterial CAT sequences in CV-1 monkey kidney cells, chicken embryo fibroblasts, Chinese hamster ovary cells, HeLa cells, and mouse HIN-3T3 cells using the Rous sarcoma virus long terminal repeat as a promoter.

(v) Enhancer Element Component

Transcription of a DNA encoding the TIE ligand homologues of the present invention by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent having been found 5' [Laimins et al., *Proc. Natl. Acad. Sci. USA* 78, 993 (1981)] and 3' [Lasky et al., *Mol Cel. Biol.* 3, 1108 (1983)] to the transcription unit, within an intron [Banerji et al., *Cell* 33, 729 (1983)] as well as within the coding sequence itself [Osborne et al., *Mol. Cel. Biol.* 4, 1293 (1984)]. Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirusearly promoter enhancer, the polyoma enhancer on the late side of the replication origin, and adenovirus enhancers. See also Yaniv, *Nature* 297, 17–18 (1982) on enhancing elements for activation of eukaryotic promoters. The enhancer may be spliced into the vector at a position 5' or 3' to the TIE ligand DNA, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding the TIE ligand. The 3' untranslated regions also include transcription termination sites.

Construction of suitable vectors containing one or more of the above listed components, the desired coding and control sequences, employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.* 9, 309 (1981) or by the method of Maxam et al., *Methods in Enzymology* 65, 499 (1980).

Particularly useful in the practice of this invention are expression vectors that provide for the transient expression in mammalian cells of DNA encoding a TIE ligand. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient systems, comprising a suitable expression vector and a host cell, allow for the convenient positive identification of polypeptides encoded by clones DNAs, as well as for the rapid screening of such polypeptides for desired biological or physiological properties. Thus, transient expression systems are particularly useful in the invention for purposes of identifying analogs and variants of a TIE ligand.

Other methods, vectors, and host cells suitable for adaptation to the synthesis of the TIE polypeptides in recombinant vertebrate cell culture are described in Getting et al., *Nature* 293, 620–625 (1981); Mantel et al., *Nature* 281, 40–46 (1979); Levinson et al.; EP 117,060 and EP 117,058. A particularly useful plasmid for mammaliancell culture expression of the TIE ligand polypeptidesis pRK5 (EP 307,247), along with its derivatives, such as, pRK5D that has an sp6 transcription initiation site followed by an SfiI restriction enzyme site preceding the Xho/NotII cDNA cloning sites, and pRK5B, a precursor of pRK5D that does not contain the SfiI site; see, Holmes et al., *Science* 253, 1278–1280 (1991).

(vii) Construction and analysis of vectors

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequences by the methods of Messing et al., *Nuclei Acids Res.* 9, 309 (1981) or by the method of Maxam et al., *Methods in Enzymology* 65, 499 (1980).

(viii) Transient expression vectors

Particularly useful in the practice of this invention are expression vectors that provide for the transient expression in mammalian cells of DNA encoding a TIE ligand. In general, transient expression involves the use of an expression vector that is able to replicate efficiently in a host cell, such that the host cell accumulates many copies of the expression vector and, in turn, synthesizes high level of a desired polypeptide encoded by the expression vector. Sambrook et al., supra, pp. 16.17–16.22. Transient expression systems, comprising a suitable expression vector and a host cell, allow for the convenient positive screening of such polypeptides for desired biological or physiological properties. Thus transient expression systems are particularly useful in the invention for purposes of identifying analogs and variants of native TIE ligand homologues with the requisite biological activity.

(ix) Suitable exemplary vertebrate cell vectors

Other methods, vectors, and host cells suitable for adaptation to the synthesis of a TIE ligand (including functional derivatives of native proteins) in recombinant vertebrate cell culture are described in Gething et al., *Nature* 293, 620–625 (1981); Mantei et al., *Nature* 281, 40–46 (1979); Levinson et al., EP 117,060; and EP 117,058. A particularly useful plasmid for mammalian cell culture expression of a TIE ligand is pRK5 (EP 307,247) or pSVI6B (PCT Publication No. WO 91/08291).

Suitable host cells for cloning or expressing the vectors herein are the prokaryote, yeast or higher eukaryote cells described above. Suitable prokaryotes include gram negative or gram positive organisms, for example *E. coli* or bacilli. A preferred cloning host is *E. coli* 294 (ATCC 31,446) although other gram negative or gram positive prokaryotes such as *E. coli* B, *E. coli* X1776 (ATCC 31,537), *E. coli* W3110 (ATCC 27,325), Pseudomonas species, or *Serratia Marcesans* are suitable.

In addition to prokaryotes, eukaryotic microbes such as filamentous fungi or yeast are suitable hosts for vectors herein. *Saccharomyces cerevisiae*, or common baker's yeast, is the most commonly used among lower eukaryotic host microorganisms. However, a number of other genera, species and strains are commonly available and useful herein, such as *S. pombe* [Beach and Nurse, *Nature* 290, 140 (1981)], *Kluvveromyces lactis* [Louvencourt et al., *J. Bacteriol.* 737(1983)]; *yarrowia* (EP402,226); *Pichia pastoris* (EP 183,070), *Trichoderma reesia* (EP 244,234), *Neurospora crassa* [Case et al., *Proc. Natl. Acad. Sci. USA* 76, 5259–5263 (1979)]; and Asperzillus hosts such as *A. nidulans* [Ballance et al., *Biochem. Biophys. Res. Commun.* 112, 284–289 (1983); Tilburn et al., *Gene* 26, 205–221 (1983); Yelton et al., *Proc. Natl. Acad. Sci. USA* 81, 1470–1474 (1984)] and *A. niger* [Kelly and Hynes, *EMBO J.* 4, 475–479 (1985)].

Suitable host cells may also derive from multicellular organisms. Such host cells are capable of complex processing and glycosylation activities. In principle, any higher eukaryotic cell culture is workable, whether from vertebrate or invertebrate culture, although cells from mammals such as humans are preferred. Examples of invertebrate cells include plants and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melangaster* (fruitfly), and *Bombyx mori* host cells have been identified. See, e.g. Luckow et al., *Bio/Technology* 6, 47–55 (1988); Miller et al., in *Genetic Engineering*, Setlow, J. K. et al., eds., Vol. 8 (Plenum Publishing, 1986), pp. 277–279; and Maeda et al., *Nature* 315, 592–594 (1985). A variety of such viral strains are publicly available, e.g. the L-1 variant of *Autorapha californica* NPV, and such viruses may be used as the virus herein according to the present invention, particularly for transfection of *Spodoptera frugiperda* cells.

Generally, plant cells are transfected by incubation with certain strains of the bacterium *Arobacterium tumefaciens*, which has been previously manipulated to contain the TIE ligand DNA. During incubation of the plant cell culture with *A. tumefaciens*, the DNA encoding a TIE ligand is transferred to the plant cell host such that it is transfected, and will, under appropriate conditions, express the TIE ligand DNA. In addition, regulatory and signal sequences compatible with plant cells are available, such as the nopaline synthase promoter and polyadenylation signal sequences. Depicker et al., *J. Mol. Appl. Gen.* 1, 561 (1982). In addition, DNA segments isolated from the upstream region of the T-DNA 780 gene are capable of activating or increasing transcription levels of plant-expressiblegenes in recombinant DNA-containing plant tissue. See EP 321,196 published Jun. 21, 1989.

However, interest has been greatest in vertebrate cells, and propagation of vertebrate cells in culture (tissue culture) is per se well known. See *Tissue Culture*, Academic Press, Kruse and Patterson, editors (1973). Examples of useful mammalian host cell lines are monkey kidney CV1 line transformned by SV40 (COS-7, ATCC CRL 1651); human embryonic kidney cell line [293 or 293 cells subcloned for growth in suspension culture, Graham el al., *J. Gen. Virol.* 36, 59 (1977)]; baby hamster kidney cells 9BHK, ATCC CCL 10); Chinese hamster ovary cells/-DHFR [CHO, Urlaub and Chasin, *Proc. Natl. Acad. Sci. USA* 77, 4216 (1980)]; mouse sertolli cells [TM4, Mather, *Biol. Reprod.* 23, 243–251 (1980)]; monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL75); human liver cells (Hep G2, HB 8065); mouse mammary tumor (MMT 060562, ATCC CCL51); TRI cells [Mather et al., *Annals N.Y. Acad. Sci.* 383, 44068 (1982)]; MRC 5 cells; FS4 cells; and a human hepatoma cell line (Hep G2). Preferred host cells are human embryonic kidney 293 and Chinese hamster ovary cells.

Particularly preferred host cells for the purpose of the present invention are vertebrate cells producing the TIE ligand homologues of the present invention.

Host cells are transfected and preferably transformed with the above-described expression or cloning vectors and cultured in conventional nutrient media modified as is appropriate for inducing promoters or selecting transformants containing amplified genes.

Prokaryotes cells used to produced the TIE ligand homologues of this invention are cultured in suitable media as describe generally in Sambrook et al., supra.

Mammalian cells can be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing the host cells. In addition, any of the media described in Ham and Wallace, *Meth. Enzymol.* 58,44(1979); Barnes and Sato, *Anal. Biochem.* 102, 255 (1980), U.S. Pat. No. 4,767,704; 4,657,866; 4,927,762; or 4,560,655; WO 90/03430; WO 87/00195 or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as GentamycinTM drug) trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH and the like, suitably are those previously used with the host cell selected for cloning or expression, as the case may be, and will be apparent to the ordinary artisan. The host cells referred to in this disclosure encompass cells in in vitro cell culture as well as cells that are within a host animal or plant.

It is further envisioned that the TIE ligand homologues of this invention may be produced by homologous recombination, or with recombinant production methods utilizing control elements introduced into cells already containing DNA encoding the particular TIE ligand.

Gene amplification and/or expression may be measured in a sample directly, for example, by conventional Southern blotting, Northern blotting to quantitate the transcription of mRNA [Thomas, *Proc. Natl. Acad. Sci. USA* 77, 5201–5205 (1980)], dot blotting (DNA analysis), or insitzi hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as a site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to the surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescentlabels, luminescent labels, and the like. A particularly sensitive staining technique suitable for use in the present invention is described by Hse et al., *Am. J. Clin. Pharm.* 75, 734–738 (1980).

Antibodies useful for immunohistochemical staining and/or assay of sample fluids may be either monoclonal or polyclonal, and may be prepared in any animal. Conveniently, the antibodies may be prepared against a native TIE ligand polypeptide of the present invention, or against a synthetic peptide based on the DNA sequence provided herein as described further hereinbelow.

The TIE ligand homologue may be produced in host cells in the form of inclusion bodies or secreted into the periplasmic space or the culture medium, and is typically recovered from host cell lysates. The recombinant ligand homologues may be purified by any technique allowing for the subsequent formation of a stable protein.

When the TIE ligand homologue is expressed in a recombinantcell other than one of human origin, it is completely free of proteins or polypeptides of human origin. However, it is necessary to purify the TIE ligand homologue from recombinant cell proteins or polypeptides to obtain preparations that are substantially homogenous as to the ligand. As a first step, the culture medium or lysate is centrifuged to remove particulate cell debris. The membrane and soluble protein fractions are then separated. The TIE ligand homologue may then be purified from the soluble protein fraction. The following procedures are exemplary of suitable purification procedures: fractionation on immuno affinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; and protein A Sepharose columns to remove contaminants such as IgG.

Functional derivatives of the TIE ligand homologues in which residues have been deleted, inserted and/or substituted are recovered in the same fashion as the native ligands, taking into account of any substantial changes in properties occasioned by the alteration. For example, fusion of the TIE ligand homologue with another protein or polypeptide, e.g. a bacterial or viral antigen, facilitates purification; an immunoaffinity column containing antibody to the antigen can be used to absorb the fusion. Immunoaffinity columns such as a rabbit polyclonal anti-TIE ligand homologue column can be employed to absorb TIE ligand homologue variants by binding to at least one remaining immune epitope. A protease inhibitor, such as phenyl methyl sulfonyl fluoride (PMSF) also may be useful to inhibit proteolytic degradation during purification, and antibioticsmay be included to prevent the growth of adventitious contaminants. The TIE ligand homologues of the present invention are conveniently purified by affinity chromatography, based upon their ability to bind to a TIE receptor, e.g. TIE-2.

One skilled in the art will appreciate that purification methods suitable for native TIE ligand homologues may require modification to account for changes in the character of a native TIE ligand homologue or its variants upon expression in recombinant cell culture.

D. Use of the TIE Ligand Homologues, Nucleic Acid Molecules and Antibodies

The TIE ligand homologues of the present invention are expected to be useful in promoting the survival and/or growth and/or differentiation of TIE receptor expressing cells in cell culture.

The TIE ligand homologues may be additionally used to identify cells which express native TIE receptors. To this end, a detectably labeled ligand is contacted with a target cell under condition permitting its binding to its receptors (TIE receptor), and the binding is monitored.

The TIE ligand homologues herein may also be used to identify molecules exhibiting a biological activity of a TIE ligand homologue, for example, by exposing a cell expressing a TIE ligand homologue herein to a test molecule, and detecting the specific binding of the test molecule to a TIE receptor, either by direct detection, or based upon secondary biological effects. This approach is particularly suitable for identifying new members of the TIE ligand family, or for screening peptide or non-peptide small molecule libraries.

The TIE ligand homologues disclosed herein are also useful in screening assays designed to identity agonists or antagonists of a native TIE receptor that play an important role in bone development, maturation or growth, or in muscle growth or development and/or promote or inhibit angiogenesis. For example, antagonists of a TIE receptor may be identified based upon their ability to block the binding of a TIE ligand homologue of the present invention to a native TIE receptor, as measured, for example, by using BiAcore biosensor technology (BIAcore; Pharmacia Biosensor, Midscataway, N.J.); or by monitoring their ability to block the biological response caused by a biologically active TIE ligand homologue herein. Biological responses that may be monitored include, for example, the phosphorylation of the TIE receptor or downstream components of the TIE signal transduction pathway, or survival, growth or differentiation of cells expressing the TIE receptor. Cell-based assays, utilizing cells that do not normally the TIE receptor, engineered to express this receptor, or to coexpress the TIE receptor and a TIE ligand homologue of the present invention, are particularly convenient to use.

In a particular embodiment, small molecule agonists and antagonists of a native TIE receptor can be identified, based upon their ability to interfere with the TIE ligand/TIE receptor interaction. There are numerous ways for measuring the specific binding of a test molecule to a TIE receptor, including, but not limited to detecting or measuring the amount of a test molecule bound to the surface of intact cells expressing the TIE receptor, cross-linked to the TIE receptor in cell lysates, or bound to the TIE receptor in vitro.

Detectably labeled TIE ligand homologues include, for example, TIE ligand homologues covalently or non-covalently linked to a radioactive substances, e.g. $^{125}I$, a fluorescent substance, a substance having enzymatic activity (preferably suitable for calorimetric detection), a substrate for an enzyme (preferably suitable for calorimetric detection), or a substance that can be recognized by a(n) (detectably labeled) antibody molecule.

The assays of the present invention may be performed in a manner similar to that described in PCT Publication WO 96/11269, published Apr. 18, 1996.

The TIE ligand homologues of the present invention are also useful for purifying TIE receptors, optionally used in the form of immunoadhesins, in which the TIE ligand or the TIE receptor binding portion thereof is fused to an immunoglobulin heavy or light chain constant region.

In addition, the new TIE ligand homologues herein can be used to promote neovascularization, and may be useful for inhibiting tumor growth.

Further potential therapeutic uses include the modulation of muscle and bone development, maturation, or growth.

The nucleic acid molecules of the present invention are useful for detecting the expression of TIE ligand homologues in cells or tissue sections. Cells or tissue sections may be contacted with a detectably labeled nucleic acid molecule encoding a TIE ligand of the present invention under hybridizing conditions, and the presence of mRNA hybridized to the nucleic acid molecule determined, thereby detecting the expression of the TIE ligand.

Antibodies of the present invention may, for example, be used in immunoassays to measure the amount of a TIE ligand in a biological sample. The biological sample is contacted with an antibody or antibody mixture specifically binding the a TIE ligand of the present invention, and the amount of the complex formed with a ligand present in the test sample is measured.

Antibodies to the TIE ligand homologues herein may additionally be used for the delivery of cytotoxic molecules, e.g. radioisotopes or toxins, or therapeutic agents to cells expressing a corresponding TIE receptor. The therapeutic agents may, for example, be other TIE ligand homologues, including the TIE-2 ligand, members of the vascular endothelial growth factor (VEGF) family, or known anti-tumor agents, and agents known to be associated with muscle growth or development, or bone development, maturation, or growth.

Anti-TIE ligand homologue antibodies are also suitable as diagnostic agents, to detect disease states associated with the expression of a TIE (e.g. TIE-2) receptor. Thus, detectably labeled TIE ligand homologues and antibody agonists of a TIE receptor can be used for imaging the presence of angiogenesis.

Anti-TIE ligand homologue antibodies specifically anti-NL6 antibodies may also find utility as anti-inflammatory agents.

For therapeutic use, the TIE ligand homologues or anti-TIE ligand antibodies of the present invention are formulated as therapeutic composition comprising the active ingredient(s) in admixture with a pharmacologically acceptable vehicle, suitable for systemic or topical application. The pharmaceutical compositions of the present invention are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG.

The active ingredients may also be entrapped in microcapsules prepared, for example, by coacervation techniques or by interfacial polymerization, for example, hydroxymethylcellulose or gelatin-microcapsules and poly-(methylmethacylate)microcapsules, respectively), in colloidal drug delivery systems (for example, liposomes, albumin microspheres, microemulsions, nano-particles and nanocapsules) or in macroemulsions. Such techniques are disclosed in *Remington's Pharmaceutical Sciences*, supra.

The formulations to be used for in vivo administration must be sterile. This is readily accomplished by filtration through sterile filtration membranes, prior to or following lyophilization and reconstitution.

Therapeutic compositions herein generally are placed into a container having a sterile access port. for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Suitable examples of sustained release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (U. Sidman et al., 1983, "Biopolymers" 22 (1): 547–556), poly (2-hydroxyethyl-methacrylate) (R. Langer, et al., 1981, "J. Biomed. Mater. Res." 15: 167–277 and R. Langer, 1982, Chem. Tech." 12: 98–105), ethylene vinyl acetate (R. Langer et al., Id.) or poly-D-(-)-3-hydroxybutyric acid (EP 133, 988A). Sustained release compositions also include liposomes. Liposomes containing a molecule within the scope of the present invention are prepared by methods known per se: DE 3,218,121A; Epstein et al., 1985, "Proc. Natl. Acad. Sci. USA" 82: 3688–3692; Hwang et al., 1980, "Proc. Natl. Acad. Sci. USA" 77: 4030–4034; EP 52322A; EP 36676A; EP 88046A; EP 143949A; EP 142641A; Japanese patent application 83-118008; U.S. Pat. Nos. 4,485,045 and 4,544, 545; and EP 102,324A. Ordinarily the liposomes are of the small (about 200–800 Angstroms) unilamelar type in which the lipid content is greater than about 30 mol. % cholesterol, the selected proportion being adjusted for the optimal NT-4 therapy.

An effective amount of a molecule of the present invention to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 $\mu$g/kg to up to 100 mg/kg or more, depending on the factors mentioned above. Typically, the clinician will administer a molecule of the present invention until a dosage is reached that provides the required biological effect. The progress of this therapy is easily monitored by conventional assays.

If the therapeutic goal is to prevent or treat tumors, the compounds herein may be combined with other therapies. For example, the patient to be treated with such anti-cancer agents may also receive radiation therapy. Alternatively, or in addition, a chemotherapeutic agent may be administered to the patient. Preparation and dosing schedules for such chemotherapeutic agents may be used according to manufacturers' instructionsor as determined empirically by the skilled practitioner. Preparation and dosing schedules for such chemotherapy are also described in *Chemotherapy Service* Ed., M. C. Perry, Williams & Wilkins, Baltimore, Md. (1992). The chemotherapeutic agent may precede, or follow administration of the anti-tumor agent, or may be given simultaneously therewith.

It may be desirable to also administer antibodies against other tumor associated antigens, such as antibodies which bind to the ErbB2, EGFR, ErbB3, ErbB4, or vascular endothelial factor (VEGF). Alternatively, or in addition, two or more antibodies binding the same or two or more different antigens disclosed herein may be co-administered to the patient. Sometimes, it may be beneficial to also administer one or more cytokines to the patient. In a preferred embodiment, the anti-tumor compounds herein are co-administered with a further growth inhibitory agent.

For the prevention or treatment of disease, the appropriate dosage of an anti-tumor agent, e.g. an antibody herein will depend on the type of disease to be treated, as defined above, the severity and course of the disease, whether the agent is administered for preventive or therapeutic purposes, previous therapy, the patient's clinical history and response to the agent, and the discretion of the attending physician. The agent is suitably administered to the patient at one time or over a series of treatments.

Further details of the invention will be apparent from the following non-limiting examples.

EXAMPLE 1

Identification of the FLS 139 Ligand

FLS139 was identified in a cDNA library prepared from human fetal liver mRNA obtained from Clontech Laboratories, Inc. Palo Alto, Calif. USA, catalog no. 64018-1, following the protocol described in "Instruction Manual: Superscript® Lambda System for cDNA Synthesis and λ cloning," cat. No. 19643-014, Life Technologies, Gaithersburg, Md., USA which is herein incorporated by reference. Unless otherwise noted, all reagents were also obtained from Life Technologies. The overall procedure can be summarized into the following steps: (1) First strand synthesis; (2) Second strand synthesis; (3) Adaptor addition; (4) Enzymatic digestion; (5) Gel isolation of cDNA; (6) Ligation into vector; and (7) Transformation.

First Strand Synthesis:

Not1 primer-adapter (LifeTech., 2 $\mu$l, 0.5 $\mu$g/$\mu$l) was added to a sterile 1.5 ml microcentrifuge tube to which was added poly A+mRNA (7 $\mu$l, 5 $\mu$g). The reaction tube was heated to 70° C. for 5 minutes or time sufficient to denature the secondary structure of the mRNA. The reaction was then chilled on ice and 5×First strand buffer (Life Tech., 4 $\mu$l), 0.1 M DTT (2 $\mu$l) and 10 mM dNTP Mix (Life Tech., 1 $\mu$l) were added and then heated to 37° C. for 2 minutes to equilibrate the temperature. Superscript II® reverse transcriptase (Life Tech., 5 $\mu$l) was then added, the reaction tube mixed well and incubated at 37° C. for 1 hour, and terminated by placement on ice. The final concentration of the reactants was the following: 50 mM Tris-HCl (pH 8.3); 75 mM KCl; 3 mM MgCl$_2$; 10 mM DTT; 500 μM each dATP, dCTP, dGTP and dTTP; 50 μg/ml Not 1 primer-adapter; 5 μg (250 μg/ml) mRNA; 50,000 U/ml Superscript II® reverse transcriptase.

Second Strand Synthesis:

While on ice, the following reagents were added to the reaction tube from the first strand synthesis, the reaction well mixed and allowed to react at 16° C. for 2 hours, taking care not to allow the temperature to go above 16° C: distilled water (93 μl); 5×Second strand buffer (30 μl); dNTP mix (3 μl); 10 U/μl E. Coli DNA ligase (1 μl); 10 U/μl E. Coli DNA polymerase I (4 μl); 2 U/μl E. Coli RNase H (1 μl). 10 U T4 DNA Polymerase (2 μl) was added and the reaction continued to incubate at 16° C for another 5 minutes. The final concentration of the reaction was the following: 25 mM Tris-HCl (pH 7.5); 100 mM KCl; 5 mM MgCl$_2$; 10 mM (NH$_4$)$_2$SO$_4$; 0.15 mM β-NAD+; 250 gM each dATP, dCTP, dGTP, dTTP; 1.2 mM DTT; 65 U/ml DNA ligase; 250 U/ml DNA polymerase I; 13 U/ml Rnase H. The reaction has halted by placement on ice and by addition of 0.5 M EDTA (10 μl), then extracted through phenol:chloroform:isoamylalcohol (25:24:1, 150 μl). The aqueous phase was removed, collected and diluted into 5M NaCl (15 μl) and absolute ethanol (−20° C., 400 μl) and centrifuged for 2 minutes at 14,000×g. The supernatant was carefully removed from the resulting DNA pellet, the pellet resuspended in 70% ethanol (0.5 ml) and centrifuged again for 2 minutes at 14,000×g. The supernatant was again removed and the pellet dried in a speedvac.

Adapter Addition

The following reagents were added to the cDNA pellet from the Second strand synthesis above, and the reaction was gently mixed and incubated at 16° C. for 16 hours: distilled water (25 μl); 5×T4 DNA ligase buffer (10 μl); Sal I adapters (10 μl); T4 DNA ligase (5 μl). The final composition of the reaction was the following: 50 mM Tris-HCl (pH 7.6); 10 mM MgCl$_2$; 1 mM ATP; 5% (w/v) PEG 8000; 1 mM DTT; 200 μg/ml Sal I adapters; 100 U/ml T4 DNA ligase. The reaction was extracted through phenol:chloroform:isoamylalcohol (25:24:1, 50 μl), the aqueous phase removed, collected and diluted into 5M NaCl (8 μl) and absolute ethanol (−20° C., 250 μl). This was then centrifuged for 20 minutes at 14,000×g, the supernatant removed and the pellet was resuspended in 0.5 ml 70% ethanol, and centrifuged again for 2 minutes at 14,000×g. Subsequently, the supernatant was removed and the resulting pellet dried in a speedvac and carried on into the next procedure.

Enzymatic Digestion

To the cDNA prepared with the Sal I adapter from the previous paragraph was added the following reagents and the mixture was incubated at 37° C. for 2 hours: DEPC-treated water (41 μl); Not 1 restriction buffer (REACT, Life Tech., 5 μl), Not 1 (4 μl). The final composition of this reaction was the following: 50 mM Tris-HCl (pH 8.0); 10 mM MgCl$_2$; 100 mM MaCl; 1,200 U/ml Not 1.

Gel Isolation of cDNA

The cDNA is size fractionated by acrylamide gel electrophoresis on a 5% acrylamide gel, and any fragments which were larger than 1 Kb, as determined by comparison with a molecular weight marker, were excised from the gel. The cDNA was then electroeluted from the gel into 0.1×TBE buffer (200 μl) and extracted with phenol:chloroform:isoamyl alcohol (25:24:1, 200 μl). The aqueous phase was removed, collected and centrifuged for 20 minutes at 14,000×g. The supernatant was removed from the DNA pellet which was resuspended in 70% ethanol (0.5 ml) and centrifuged again for 2 minutes at 14,000×g. The supernatant was again discarded, the pellet dried in a speedvac and resuspended in distilled water (15 μl).

Ligation of cDNA into pRK5 Vector

The following reagents were added together and incubated at 16° C. for 16 hours: 5×T4 ligase buffer (3 μl); pRK5, Xho1, Not1 digested vector, 0.5 μg, 1 μl); cDNA prepared from previous paragraph (5 μl) and distilled water (6 μl). Subsequently, additional distilled water (70 μl) and 10 mg/ml tRNA (0.1 μl) were added and the entire reaction was extracted through phenol:chloroforrn:isoamyl alcohol (25:24:1). The aqueous phase was removed, collected and diluted into 5M NaCl (10 μl) and absolute ethanol (−20° C., 250 μl). This was then centrifuged for 20 minutes at 14,000× g, decanted, and the pellet resuspended into 70% ethanol (0.5 ml) and centrifuged again for 2 minutes at 14,000×g. The DNA pellet was then dried in a speedvac and eluted into distilled water (3 μl) for use in the subsequent procedure.

Transformation of Library Ligation into Bacteria

The ligated cDNA/pRK5 vector DNA prepared previously was chilled on ice to which was added electrocompetent DH10B bacteria (Life Tech., 20 μl). The bacteria vector mixture was then electroporated as per the manufacturers recommendation. Subsequently SOC media (1 ml) was added and the mixture was incubated at 37° C. for 30 minutes. The transformants were then plated onto 20 standard 150 mm LB plates containing ampicillin and incubated for 16 hours (370° C.) to allow the colonies to grow. Positive colonies were then scraped off and the DNA isolated from the bacterial pellet using standard CsCl-gradient protocols. For example, Ausubel et al., 2.3.1.

Identification of FLS 139

FLS139 can be identified in the human fetal liver library by any standard method known in the art, including the methods reported by Klein R. D. et al. (1996), *Proc. Natl. Acad. Sci.* 93, 7108–7113 and Jacobs (U.S. Pat. No. 5,563, 637 issued Jul. 16, 1996). According to Klein et al. and Jacobs, cDNAs encoding novel secreted and membrane-bound mammalian proteins are identified by detecting their secretory leader sequences using the yeast invertase gene as a reporter system. The enzyme invertase catalyzes the breakdown of sucrose to glucose and fructose as well as the breakdown of raffinose to sucrose and melibiose. The secreted form of invertase is required for the utilization of sucrose by yeast (*Saccharomyces cerevisiae*) so that yeast cells that are unable to produce secreted invertase grow poorly on media containing sucrose as the sole carbon and energy source. Both Klein R. D., supra, and Jacobs, supra, take advantage of the known ability of mammalian signal sequences to functionally replace the native signal sequence of yeast invertase. A mammalian cDNA library is ligated to a DNA encoding a nonsecreted yeast invertase, the ligated DNA is isolated and transformed into yeast cells that do not contain an invertase gene. Recombinants containing the nonsecreted yeast invertase gene ligated to a mammalian signal sequence are identified based upon their ability to grow on a medium containing only sucrose or only raffinose as the carbon source. The mammalian signal sequences identified are then used to screen a second, full-length cDNA library to isolate the full-length clones encoding the corresponding secreted proteins. Cloning may, for example, be performed by expression cloning or by any other technique known in the art.

The primers used for the identification of FL139 are as follows:

```
OLII14  CCACGTTGGCTTGAAATTGA                                         SEQ. ID. NO: 13

OLII15  CCTCCAGAATTGATCAAGACAATTCATGATTTGATTCTCTATCTCCAGAG           SEQ. ID. NO: 14

OLII16  TCGTCTAACATAGCAAATC                                          SEQ. ID. NO:15
```

The nucleotidesequence of FLS139 in shown in FIG. 6 (SEQ. ID. NO: 5), while its amino acid sequence is shown in FIG. 7 (SEQ. ID. NO:6). As illustrated in FIG. 1, FLS139 contains a fibrinogen-like domain exhibiting a high degree of sequence homology with the two known human ligands of the TIE-2 receptor (h-TIE2L1 and h-TIE2L2). Accordingly, FLS 139 has been identified as a novel member of the TIE ligand family.

A clone of FLS139 was deposited with the American Type Culture Collection (ATCC), 10801 University Boulevard, Manassas Va. 20110-2209, on Sep. 18, 1997 under the terms of the Budapest Treaty, and has been assigned the deposit number ATCC 209281.

EXAMPLE 2

Identification of NL2 and NL3

NL2 and NL3 were by screening the GenBank database using the computer program BLAST (Altshul et al., *Methods in Enzymology* 266:460–480 (1996). The NL2 sequence shows homology with known EST sequences T08223, AA122061,and M62290. Similarly, NL3 shows homology with the known EST sequences T57280, and T50719. None of the known EST sequences have been identified as full length sequences, or described as ligands associated with the TIE receptors.

Following their identification, NL2 and NL3 were cloned from a human fetal lung library prepared from mRNA purchased from Clontech, Inc. (Palo Alto, Calif., USA), catalog # 6528-1, following the manufacturer's instructions. The library was screened by hybridization with synthetic oligonucleotide probes:

18, 1997 under the terms of the Budapest Treaty, and has been assigned the deposit number ATCC 209284.

A clone of NL3 was deposited with the American Type Culture Collection (ATCC), 10801 University Boulevard, Manassas Va. 20110-2209, on Sep. 18, 1997 under the terms of the Budapest Treaty, and has been assigned the deposit number ATCC 209283.

EXAMPLE 3

Northern Blot Analysis and in situ Hybridization Results

Expression of the FLS139, NL2 and NL3 mRNA in human tissues was examined by Northern blot analysis. Human mRNA blots were hybridized to a $^{32}$P-labeled DNA probe based on the full length cDNAs; the probes were generated by digesting and purifying the cDNA inserts. Human fetal RNA blot MTN (Clontech) and human adult RNA blot MTN-III (Clontech)were incubated with the DNA probes. Blots were incubated with the probes in hybridization buffer (5×SSPE; 2Denhardt's solution; 100 mg/mL denatured sheared salmon sperm DNA; 50% formamide; 2% SDS) for 60 hours at 42° C. The blots were washed several times in 2×SSC; 0.05% SDS for 1 hour at room temperature, followed by a 30 minute wash in 0.1×SSC; 0.1% SDS at 50° C. The blots were developed after overnight exposure by phosphorimager analysis (Fuji).

Figure 8:
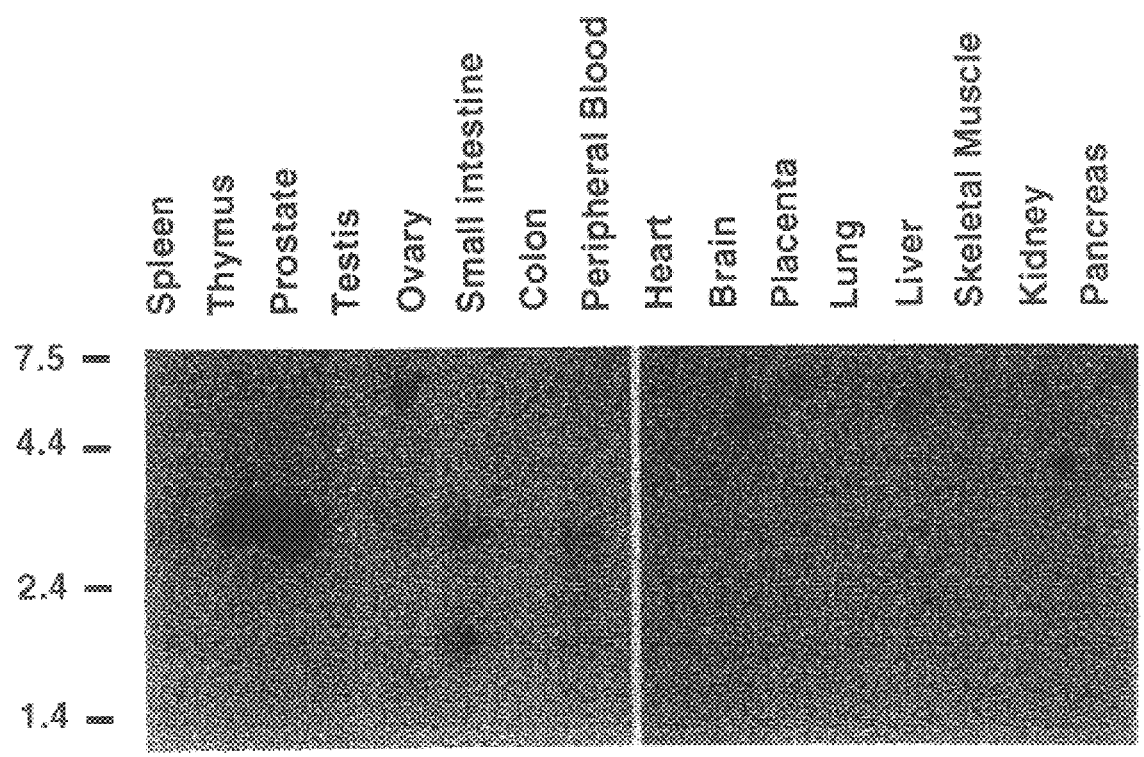
FIG. 8–9—Northern blots showing the expression of the mRNAs of TIE ligand homologues NL2 and NL3 in various tissues.
Figure 9:
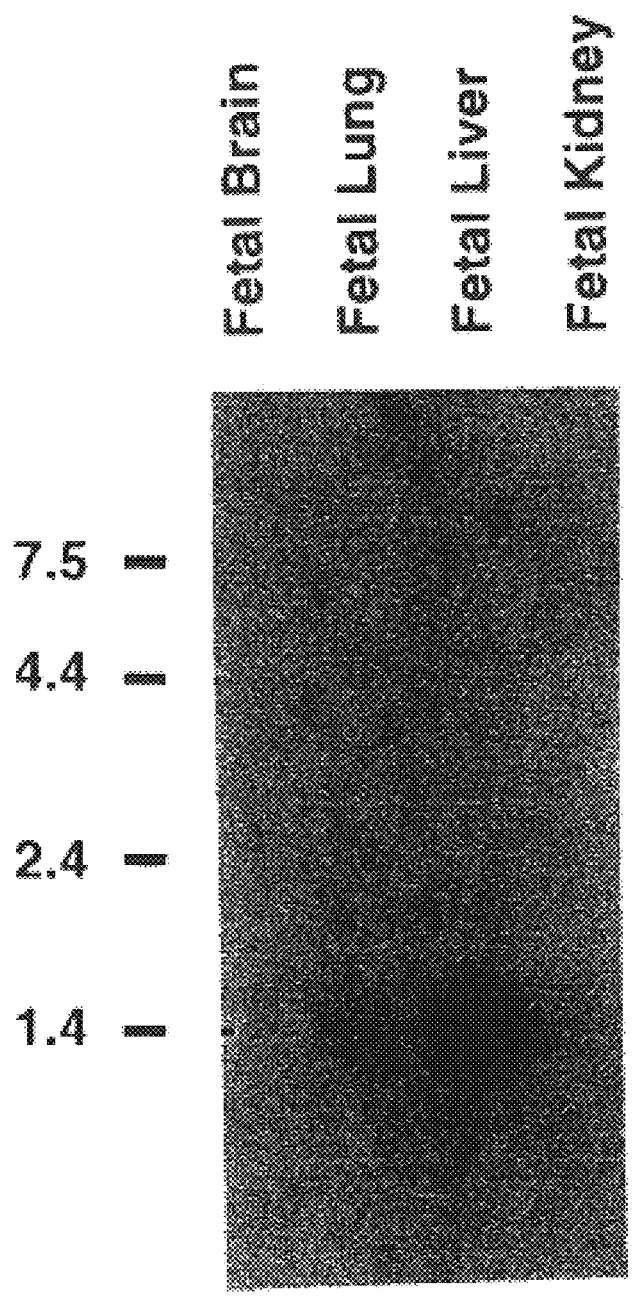

As shown in FIGS. 8 and 9, NL2 and NL3 mRNA transcripts were detected.

The tissue expression pattern of NL3 was also determined by in situ hybridization (observing hybridization to cellular RNA), using an optimized protocol that employs PCR-generated $^{33}$P-labeled riboprobes. (Lu and Gillett, *Cell*

```
For NL2:
NL2,5-1  ATGAGGTGGCCAAGCCTGCCCGAAGAAAGAGGC         SEQ. ID. NO: 7

NL2,3-1  CAACTGGCTGGGCCATCTCGGGCAGCCTCTTTCTTCGGG   SEQ. ID. NO: 8

NL2,3-4  CCCAGCCAGAACTCGCCGTGGGGA                  SEQ. ID. NO: 9

For NL3:
NL3,5-1  TGGTTGGCAAAGGCAAGGTGGCTGACGATCCGG         SEQ. ID. NO: 10

NL3,3-1  GTGGCCCTTATCTCTCCTGTACAGCTTCCGGATCGTCAGCCAC  SEQ. ID. NO: 11

NL3,3-2  TCCATTCCCACCTATGACGCTGACCCA               SEQ. ID. NO: 12
``` based on the ESTs found in the GenBank database. cDNA sequences were sequences in their entireties.

The nucleotide and amino acid sequences of NL2 are shown in FIG. 2 (SEQ. ID. NO: 1) and FIG. 3 (SEQ. ID. NO: 2), respectively. The nucleotide and amino acid sequences of NL3 are shown in FIG. 4 (SEQ. ID. NO: 3) and FIG. 5 (SEQ. ID. NO: 4), respectively.

A clone of NL2 (NL2-DNA 22780-1078)was deposited with the American Type Culture Collection (ATCC), 10801 University Boulevard, Manassas Va. 20110-2209, on Sep.

*Vision* 1: 169–176 (1994)). Formalin-fixed, paraffin-embedded human fetal and adult tissues were sectioned, deparaffinized, deproteinated in proteinase K (20 g/ml) for 15 minutes at 37° C., and further processed for in situ hybridization as described by Lu and Gillett (1 994). A [$^{33}$-P] UTP-labeled antisense riboprobe was generated from a PCR product and hybridized at 55° C. overnight. The slides were dipped in Kodak NTB2 nuclear track emulsion and exposed for 4 weeks.

³³P-Riboprobe synthesis 6.0 µl (125 mCi) of ³³P-UTP (Amersham BF 1002, SA<2000 Ci/mmol) were speed vac dried. To each tube containing dried ³³P-UTP, the following ingredients were added:

- 2.0 µl 5×transcription buffer
- 1.0 µl DTT (100 mM)
- 2.0 µl NTP mix (2.5 mM: 10 µ; each of 10 mM GTP, CTP & ATP+10 µl H₂O)
- 1.0 µl UTP (50 µM)
- 1.0 µl Rnasin
- 1.0 µl DNA template (1 µg)
- 1.0 µl H₂O
- 1.0 µl RNA polymerase (for PCR products T3=AS, T7=S, usually)

The tubes were incubated at 37° C. for one hour. 1.0 µl RQ1 DNase were added, followed by incubation at 37° C. for 15 minutes. 90 µl TE (10 mM Tris pH 7.6/1 mM EDTA pH 8.0) were added, and mixture was pipetted onto DES81 paper. The remaining solution was loaded in a Microcon-50 tissue was covered with 50 µl of hybridization buffer (3.75 g Dextran Sulfate+6 ml SQ H₂O), vortexed and heated in the microwave for 2 minutes with the cap loosened. Aftercooling on ice, 18.75 ml formamide, 3.75 ml 20×SSC and 9 ml SQ H₂O were added, the tissue was vortexed well, and incubated at 42° C. for 1–4 hours.

Hybridization 1.0×10⁶ cpm probe and 1.0 µl tRNA (50 mg/ml stock) per slide were heated at 95° C. for 3 minutes. The slides were cooled on ice, and 48 µg hybridization buffer were added per slide. After vortexing, 50 µl ³³P mix were added to 50 µl prehybridization on slide. The slides were incubated overnight at 55° C.

Washes

Washing was done 2×10 minutes with 2×SSC, EDTA at room temperature (400 ml 20×SSC+16 ml 0.25M EDTA, $V_f$=4L), followed by RNaseA treatment at 37° C. for 30 minutes (500 µof 10 mg/ml in 250 ml Rnase buffer=20 µg/ml), The slides were washed 2×10 minutes with 2×SSC, EDTA at room temperature. The stringency wash conditions were as follows: 2 hours at 55° C., 0.1×SSC, EDTA (20 ml 20×SSC+16 ml EDTA, $V_f$=4 L).

```
C-141F-NL3p1:48mer   GGA TTC TAA TAC GAC TCA CTA TAG GGC AAG TTG TCC TCC   (SEQ ID NO:16)

C-141G-NL3p2:47mer   CTA TGA AAT TAA CCC TCA CTA AAG GGA CGT GGT CAG CGT   (SEQ ID NO: 17)
``` ultrafiltration unit, and spun using program 10 (6 minutes). The filtration unit was inverted over a second tube and spun using program 2 (3 minutes). After the final recovery spin, 100 µl TE were added. 1 µl of the final product was pipetted on DE81 paper and counted in 6 ml of Biofluor II.

The probe was run on a TBE/urea gel. 1–3 µl of the probe or 5 µl of RNA Mrk III were added to 3 µl of loading buffer. After heating on a 95° C. heat block for three minutes, the gel was immediately placed on ice. The wells of gel were flushed, the sample loaded, and run at 180–250 volts for 45 minutes. The gel was wrapped in saran wrap and exposed to XAR film with an intensifying screen in –70° C. freezer one hour to overnight.

³³P-Hybridization

Pretreatment of Frozen Sections

The slides were removed from the freezer, placed on aluminium trays and thawed at room temperature for 5 minutes. The trays were placed in 55° C. incubator for five minutes to reduce condensation. The slides were fixed for 10 minutes in 4% paraformaldehyde on ice in the fume hood, and washed in 0.5×SSC for 5 minutes, at room temperature (25 ml 20×SSC+975 ml SQ H₂O). After deproteination in 0.5 µg/ml proteinase K for 10 minutes at 37° C. (12.5 µl of 10 mg/ml stock in 250 ml prewarmed RNase-free RNAse buffer), the sections were washed in 0.5×SSC for 10 minutes at room temperature. The sections were dehydrated in 70%, 95%, 100% ethanol, 2 minutes each.

Pretreatment of Paraffin-embedded Sections

The slides were deparaffinized, placed in SQ H₂O, and rinsed twice in 2×SSC at room temperature, for 5 minutes each time. The sections were deproteinated in 20 µg/ml proteinase K (500 µl of 10 mg/ml in 250 ml RNase-free RNase buffer; 37° C., 15 minutes)—human embryo, or 8×proteinase K (100 µl in 250 ml Rnase buffer, 37° C, 30 minutes)—formalin tissues. Subsequent rinsing in 0.5×SSC and dehydration were performed as described above.

Prehybridization

The slides were laid out in plastic box lined with Box buffer (4×SSC, 50% formamide)—saturated filter paper. The The adult tissues examined were: liver, kidney, adrenal, myocardium, aorta, spleen, lympho node, pancreas, lung, skin, cerebral cortex, hippocampus, cerebellum, penis, eye, bladder, stomach, gastric carcinoma, colon, colonic carcinomsa and chondrosarcoma, acetominophen induced liver injury and hepatic cirrhosis. Fetal tissues examinedwere: planceta, umbilicalcord, liver, kidney, adrenals,thyorid, lungs, heart, great vessels, oesophagus, stomach, small intestine, spleen, thymus, pancreas, brain, eye, spinal cord, body wall, penvis and lower limb. Expression was not observed in any of the normal or fetal tissues. Expression was detected in hepatic sinusoidal cells (probably endothelial) in both acute (acetaminophen induced) and chronic hepatic injury (cirrhosis and adjacent to colorectal carcinoma metastasis). These results indicate that NL3 may play a role in the regulation of hepatic regeneration.

The expression of NL1 was also examined in a similar array of adult and fetal tissues but no expressed was observed under the conditions indicated above.

EXAMPLE 4

Expression of FLS139. NL2 and NL3 in *E. coli*

This example illustrates the preparation of an unglycosylated form of the TIE ligand homologues of the present invention in *E. coli*. The DNA sequence encodingaNL-2, NL-3 or FLS139ligand (SEQ. ID. NOs: 1, 3, and 5, respectively) is initially amplified using selected PCR primers. The primers should contain restriction enzyme sites which correspond to the restriction enzyme sites on the selected expression vector. A variety of expression vectors may be employed. The vector will preferably encode an antibiotic resistance gene, an origin of replication, e promoter, and a ribozyme binding site. An example of a suitable vector is pBR322 (derived from *E. coli*; see Bolivar et al., *Gene* 2:95 (1977)) which contains genes for ampicillin and tetracycline resistance. The vector is digested with restriction enzyme and dephosphorylated. The PCR amplified sequences are then ligated into the vector.

The ligation mixture is then used to transform a selected *E. coli* strain, using the methods described in Sambrook et al., supra. Transformants are identified by their ability to grow on LB plates and antibiotic resistant colonies are then selected. Plasmid DNA can be isolated and confirmed by restriction analysis.

Selected clones can be grown overnight in liquid culture medium such as IB broth supplemented with antibiotics. The overnight culture may subsequently be used to inoculate a later scale culture. The cells are then grown to a desired optical density. An inducer, such as IPTG may be added.

After culturing the cells for several more hours, the cells can be harvested by centrifugation. The cell pellet obtained by the centrifugation can be solubilized using various agents known in the art, and the solubilized protein can then be purified using a metal chelating column under conditions that allow tight binding of the protein.

Indeed, NL2 was expressed in E. coli in a poly-His tagged form, using the following procedure. The DNA encoding NL2 was initially amplified using selected PCR primers. The primers contained restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequence was then ligated into an expression vector, which was used to transform an E. coli host based on strain 52 (W3110 fuhA (tonA) lon galE rpoHts(htpRts) clpP(lacIq)). Transformants were first grown in LB containing 50 mg/ml carbenicillinat 30° C. with shaking until an O.D.600 of 3–5 was reached. Cultures were then diluted 50–100 fold into CRAP media (prepared by mixing 3.57 g $(NH_4)_2SO_4$, 0.71 g sodium citrate.2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20–30 hours at 30° C. with shaking. Samples were removed to verify expression by SDS-PAGE analysis, and the bulk culture is centrifuged to pellet the cells. Cell pellets were frozen until purification and refolding.

E. coli paste from 0.5 to 1 L fermentations (6–10 g pellets) was resuspended in 10 volumes (w/v) in 7 M guanidine, 20 mM Tris, pH 8 buffer. Solid sodium sulfite and sodium tetrathionate was added to make final concentrations of 0.1M and 0.02 M, respectively, and the solution was stirred overnight at 4° C. This step results in a denatured protein with all cysteine residues blocked by sulfitolization. The solution was centrifuged at 40,000 rpm in a Beckman Ultracentifuge for 30 min. The supernatant was diluted with 3–5 volumes of metal chelate column buffer (6 M guanidine, 20 mM Tris, pH 7.4) and filtered through 0.22 micron filters to clarify. Depending the clarified extract was loaded onto a 5 ml Qiagen Ni-NTA metal chelate column equilibrated in the metal chelate column buffer. The column was washed with additional buffer containing 50 mM imidazole (Calbiochem, Utrol grade), pH 7.4. The protein was eluted with buffer containing 250 mM imidazole. Fractions containing the desired protein were pooled and stored at 4° C. Protein concentration was estimated by its absorbance at 280 nm using the calculated extinction coefficient based on its amino acid sequence.

The protein was refolded by diluting sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes were chosen so that the final protein concentration was between 50 to 100 micrograms/ml. The refolding solution was stirred gently at 4° C. for 12–36 hours. The refolding reaction was quenched by the addition of TFA to a final concentration of 0.4% (pH of approximately 3). Before further purification of the protein, the solution was filtered through a 0.22 micron filter and acetonitrile was added to 2–10% final concentration. The refolded protein was chromatographed on a Poros R1/H reversed phase column using a mobile buffer of 0.1% TFA with elution with a gradient of acetonitrile from 10 to 80%. Aliquots of fractions with A280 absorbance were analyzed on SDS polyacrylamide gels and fractions containing homogeneous refolded protein were pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded NL2 protein were pooled and the acetonitrile removed using a gentle stream of nitrogen directed at the solution. Proteins were formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

EXAMPLE 5

Expression of FLS139. NL2 and NL3 in mammalian cells

This example illustrates preparation of a glycosylated form of the FLS139, NL2 and NL3 ligand homologues by recombinant expression in mammalian cells.

The vector, pRK5 (see EP 307,247, published Mar. 15, 1989), is employed as the expression vector. Optionally, the FLS139,NL2 and NL3 DNA is ligated into pRK5 with selected restriction enzymes to allow insertion of the FLS139, NL2 and NL3 DNA using ligation methods such as described in Sambrook et al., supra. The resulting vector is called pRK5-FLS139, -NL2 and NL3, respectively.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 µg pRK5-FLS139, -NL2 and NL-3 DNA is mixed with about 1 µg DNA encoding the VA RNA gene [Thimmappaya et al., Cell, 31:543 (1982)] and dissolved in 500 µl of 1 mM Tris-HCl, 0.1 mM EDTA, 0.227M $CaCl_2$. To this mixture is added, dropwise, 500 µl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 µCi/ml $^{35}$S-cysteine and 200 µCi/ml $^3$S-methionine. After a 12 hour incubation, the conditioned medium is collected, concentrated on a spin filter, and loaded onto a 15% SDS gel. The processed gel may be dried and exposed to film for a selected period of time to reveal the presence of FLS139, NL2 and NL3 polypeptide. The cultures containing transfected cells may undergo further incubation (in serum free medium) and the medium is tested in selected bioassays.

In an alternative technique, FLS139, NL2 and NL3 may be introduced into 293 cells transiently using the dextran sulfate method described by Somparyrac et al., *Proc. Natl. Acad. Sci.*, 12:7575 (1981). 293 cells are grown to maximal density in a spinner flask and 700 µg pRK5-FLS 139, -NL2 and -NL3 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing expressed FLS139, NL2 and NL3 can then be concentrated and purified by any selected method, such as dialysis and/or column chromatography.

In another embodiment, FLS139, NL2 and NL3 can be expressed in CHO cells. The pRK5-FLS139, -NL2 and -NL3 can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of FLS139, NL2 and NL3 polypeptide, the culture medium may be replaced with serum free medium. Preferably, the cultures are incubated for about 6 days, and then the conditioned medium is harvested. The medium containing the expressed FLS139, NL2 and NL3 can then be concentrated and purified by any selected method.

Epitope-tagged FLS139, NL2 and NL3 may also be expressed in host CHO cells. FLS139, NL2 and NL3 may be subcloned out of the pRK5 vector. The subcloned insert can undergo PCR to fuse in frame with a selected epitope tag such as a poly-his tag into a Baculovirus expression vector. The poly-his tagged FLS139, NL2 and NL3 insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged FLS139, NL2 and NL3 can then be concentrated and purified by any selected method, such as by $Ni^{2+}$-chelate affinity chromatography.

Glycosylated forms of NL2, NL3 and FLS139 (NL6) were indeed expressed in CHO cells in poly-His tagged forms. Following PCR amplification, the NL2, NL3 or NL6 DNA was subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used for the expression of NL2, NL3 or NL6 in CHO cells is as described in Lucas et al., *Nucl. Acids Res.* 24:9 (1774–1779(1996), and uses the SV40 early promoter/enhancer to drive expression of the cDNA of interest and dihydrofolate reductase (DHFR). DHFR expression permits selection for stable maintenance of the plasmid following transfection.

Twelve micrograms of NL2-, NL3- or NL6-encoding plasmid DNA were introduced into approximately 10 million CHO cells using commercially available transfection reagents Superfect® (Quiagen), Dosper® or Fugene® (Boehringer Mannheim). The cells were grown and described in Lucas et al., supra. Approximately $3 \times 10^{-7}$ cells were frozen in an ampoule for further growth and production as described below.

The ampoule containing NL2, NL3 or NL6 plasmid DNA was thawed by placement into water bath and mixed by vortexing. The contents were pipetted into a centrifuge tube containing 10 mLs of medium and centrifuged at 1000 rpm for 5 minutes. The supernatant was aspirated and the cells were resuspended in 10 mL of selective medium (0.2 µm filtered PS20 with 5% 0.2 µm diafiltered fetal bovine serum). The cells were then aliquoted into a 100 mL spinner containing 90 mL of selective medium. After 1–2 days, the cells were transferred into a 250 mL spinner filled with 150 mL selective growth medium and incubated at 37° C. After another 2–3 days, a 250 mL, 500 mL and 2000 mL spinners were seeded with $3 \times 10^5$ cells/mL. The was exchanged with fresh medium by centrifugation and resuspension in production medium. Any suitable CHO medium may be employed, e.g., such as is described in U.S. Pat. No. 5,122,469, issued Jun. 16, 1992. A 3L production spinner is seeded at $1.2 \times 10^6$ cells/mL. On day 0, the cell number and pH were determined. On day 1, the spinner was sampled and sparging with filtered air was commenced. On day 2, the spinner was sampled, the temperature shifted to 33° C., and 30 mL of 500 g/L-glucose and 0.6 mL of 10% antifoam (e.g., 35% polydimethylsiloxane emulsion, Dow Corning 365 Medical Grade Emulsion) were added. Throughout the production, pH was adjusted as necessary to keep at around 7.2. After 10 days, or until viability dropped below 70%, the cell culture was harvested by centrifugation and filtered through a 0.22 µm filter. The filtrate was either stored at 4° C. until loading onto a purification column.

The poly-His tagged were purified using a Ni-NTA column (Qiagen). Before purification, imidazole was added to the conditioned medium to a concentration of 5 mM. The conditioned medium was pumped onto a 6 ml Ni-NTA column equilibrated in 20 mM Hepes, pH 7.4, buffer containing 0.3 M NaCl and 5 mM imidazole at a flow rate of 4–5 ml/min. at 4° C. After loading, the column was washed with additional equilibration buffer and the protein eluted with equilibration buffer containing 0.25 M imidazole. The purified protein was subsequently desalted into a storage buffer containing 10 mM Hepes, 0.14 M NaCl and 4% mannitol, pH 6.8, with a 25 ml G25 Superfine (Pharmacia) column and stored at −80° C.

The homogeneity of the purified proteins was confirmed by SDS PEG and N-terminal amino acid sequencing performed by Edman degradation.

EXAMPLE 6

Expression of FLS139, NL2 and NL3 in yeast

First, yeast expression vectors are constructed for intracellular production or secretion of FLS139, NL2 and NL3 from the ADH2/GAPDH promoter. DNA encoding FLS139, NL2 and NL3, a selected signal peptide and the promoter is inserted into suitable restriction enzyme sites in the selected plasmid to direct intracellular expression of FLS139, NL2 and NL3. For secretion, DNA encoding FLS139, NL2 and NL3 can be cloned into the selected plasmid, together with DNA encoding the ADR2/GAPDH promoter, the yeast alpha-factor secretory signal/leader sequence, and linker sequences (if needed) for expression of FLS139, NL2 and NL3.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant FLS139, NL2 and NL3 can subsequently be isolated and purified by removing the yeast cells from the fermentation medium by centrifugation and then concentrating the medium using selected cartridge filters. The concentrate containing FLS139, NL2 and NL3 may further be purified using selected column chromatography resins.

EXAMPLE 7

Expression of FLS139, NL2 and NL3 in Baculovirus transfected Insect Cells

The following method describes recombinant expression of FLS139, NL2 and NL3 in Baculovirus transfected insect cells.

The FLS139, NL2 and NL3 is fused upstream of an epitope tag contained with a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the FLS139, NL2 and NL3 or the desired portion of the FLS139, NL2 and NL3 (such as the sequence encoding the extracellular domain of a transmembrane protein) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4–5 days of incubation at 28° C, the released viruses are harvested and used for further amplifications. Viral infection and protein expression is performed as described by O'Reilley et al., Baculovirus expression vectors: A laboratory Manual, Oxford: Oxford University Press (1994).

Expressed poly-his tagged FLS139, NL2 and NL3 can then be purified, for example, by $Ni^{2+}$-chelate affinity chromatographyas follows. Extracts are prepared from recombinantvirus-infected Sf9 cells as described by Rupert et al., Nature, 362:175–179 (1993). Briefly, Sf9 cells are washed, resuspended in sonication buffer (25 mL Hepes, pH 7.9; 12.5 mM $MgCl_2$; 0.1 mM EDTA; 10% Glycerol; 0.1% NP-40; 0.4 M KCl), and sonicated twice for 20 seconds on ice. The sonicates are cleared by centrifugation, and the supematant is diluted 50-fold in loading buffer (50 mM phosphate, 300 mM NaCl, 10% Glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% Glycerol, pH 6.0), which elutes non-specifically bound protein. After reaching $A_{280}$ baseline again, the column is developed with a 0 to 500 mM Imidazole gradient in the secondary wash buffer. One mL fractions are col lected and analyzed by SDS-PAGE and silver staining or western blot with $Ni^{2+}$-NTA-conjugated to alkaline phosphatase (Qiagen). Fractions containing the eluted $His_{10}$-tagged FLS 139, NL2 and NL3 are pooled and dialyzed against loading buffer.

Alternatively, purification of the IgG tagged (or Fc tagged) FLS139, NL2 and NL3 can be performed using known chromatography techniques, including for instance, Protein A or protein G column chromatography.

NL2 and FLS139 (NL6) were expressed in Baculovirus-infected HighS cells in poly-His tagged forms. While the expression was actually performed in a 0.5 L scale, it can be readily scaled up for larger (e.g. 8 L) preparations.

Following PCR amplification of the respective coding sequences were subcloned into a baculovirus expression vector (pb.PH.His.c), and the vector and Baculogold® baculovirus DNA (Pharmingen) were co-transfected into Highs cells, using Lipofectin (Gibco BRL). pb.PH.His is a modification of the commercially available baculovirus expression vector pVL1393 (Pharmingen), with a modified polylinker region to include the His sequences. The cells were grown in Hink's TNM-FH medium supplemented with 10% FBS (Hyclone). Cells were incubated for 5 days at 28° C. The supernatant was harvested and subsequently used for the first viral amplification by infecting Sf9 cells in Hink's TNM-FH medium supplemented with 10% FBS at an approximate multiplicity of infection (MOI) of 10. Cells were incubated for 3 days at 28° C. The supernatant was harvested and the expression of the NL2 and NL6 constructs in the baculovirus expression vector was determined by batch binding of I ml of supernatant to 25 mL of Ni-NTA beads (QIAGEN) followed by SDS-PAGE analysis comparing to a known concentration of protein standard by Coomassie blue staining.

The first viral amplification supernatant was used to infect a spinner culture (500 ml) of High5 cells grown in ESF-921 medium (Expression Systems LLC) at an approximate MOI of 0.1. Cells were incubated for 3 days at 28° C. The supernatant was harvested and filtered. Batch binding and SDS-PAGE analysis was repeated, as necessary, until expression of the spinner culture was confirmed.

The conditioned medium from the transfected cells (0.5 to 3 L) was harvested by centrifugation to remove the cells and filtered through 0.22 micron filters. The poly-His tagged constructs were purified using a Ni-NTA column (Qiagen). Before purification, imidazole was added to the conditioned media to a concentration of 5 mM. The conditioned media were pumped onto a 6 ml Ni-NTA column equilibrated in 20 mM Hepes, pH 7.4, buffer containing 0.3 M NaCl and 5 mM imidazole at a flow rate of 4–5 ml/min. at 4° C. After loading, the column was washed with additional equilibration buffer and the protein eluted with equilibration buffer containing 0.25 M imidazole. The highly purified protein was subsequently desalted into a storage buffer containing 10 mM Hepes, 0.14 M NaCl and 4% mannitol, pH 6.8, with a 25 ml G25 Superfine (Pharmacia) column and stored at −80° C.

The homogeneity of the NL2 and NL6 proteins was verified by SDS polyacrylamide gel (PEG) electrophoresis and N-terminal amino acid sequencing by Edman degradation.

EXAMPLE 8

Preparation of Antibodies that bind FLS139, NL2, or NL3

This example illustrates preparation of monoclonal antibodies which can specifically bind FLS139, NL2, or NL3.

Techniques for producing the monoclonal antibodies are known in the art and are described, for example, in Goding, supra. Immunogens that may be employed include purified ligand homologues of the present invention, fusion proteins containing such ligand homologues, and cells expressing recombinant ligand homologues on the cell surface. Selection of the immunogen can be made by the skilled artisan without undue experimentation.

Mice, such as Balb/c, are immunized with the immunogen emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, Mont.) and injected into the animal's hind food pads. The immunized mice are then boosted 10 to 12 days later with additional immunogen emulsified in the selected adjuvant. Thereafter, for several weeks, the mice might also be boosted with additional immunization injections. Serum samples may be periodically obtained from the mice by retro-orbital bleeding for testing ELISA assays to detect the antibodies.

After a suitable antibody titer has been detected, the animals "positive" for antibodies can be injected with a final intravenous injection of the given ligand. Three to four days later, the mice are sacrificed and the spleen cells are harvested. The spleen cells are then fused (using 35% polyethylene glycol) to a selected murine myeloma cell line such as P3X63AgU. 1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against the antigen. Determination of "positive" hybridoma cells secreting the desired monoclonal antibodies against the TIE ligand homologues herein is well within the skill in the art.

The positive hybridoma cells can be injected intraperitoneal into syngeneic Balb/c mice to produce ascites containing the anti-TIE-ligand monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

EXAMPLE 9

Inhibition of VEGF stimulated endothelial cell proliferation

Bovine adrenal cortical capillary endothelial (ACE) cells (from primary culture, maximum 12–14 passages) were plated on 96-well microtiter plates (Amersham Life Science) at a density of 500 cells/well per 100 μL in low glucose DMEM, 10% calf serum, 2 mM glutamine, 1×pen/strept and fungizone, supplemented with 3 ng/mL VEGF. Controls were plated the same way but some did not include VEGF. Test samples of the NL8 polypeptide were added in a 100 μl volume for a 200 mcL final volume. Cells were incubated for 6–7 days at 37° C. The medium was aspirated and the cells washed 1× with PBS. An acid phosphatase reaction mixture (100 μL, 0.1 M sodium acetate, pH 5.5, 0.1% Triton-100, 10 mM p-nitrophenyl phosphate) was added. After incubation for 2 hours at 37° C., the reaction was stopped by addition of 10 mcL 1N NaOH. OD was measured on microtiter plate reader at 405 nm. Controls were no cells, cells alone, cells +FGF (5 ng/mL), cells+VEGF (3 ng/mL), cells+VEGF (3 ng/ml)+TGF-β (1 ng/ml), and cells+VEGF (3 ng/mL)+LIF (5 ng/mL). (TGF-β at a 1 ng/ml concentration is known to block 70–90% of VEGF stimulated cell proliferation.)

The results were assessed by calculating the percentage inhibition of VEGF (3 ng/ml) stimulated cell proliferation, determined by measuring acid phosphatase activity at OD405 nm, (1) relative to cells without stimulation, and (2) relative to the reference TGF-β inhibition of VEGF stimulated activity. The results are considered positive, if the inhibition is 30% or greater. The results shown in Table 1 below are indicative of the utility NL2, NL6, and possibly related polypeptides, in cancer therapy and specifically in inhibiting tumor angiogenesis. The numerical values (relative inhibition) shown in Table 1 were determined by calculating the percent inhibition of VEGF stimulated proliferation by the tested TIE ligand homologues relative to cells without stimulation and then dividing the percentage into the percent inhibition obtained by TGF-β at 2 ng/ml which is known to block 70–90% of VEGF stimulated cell proliferation.

TABLE 2

| Protein Name | Protein Concentration | Relative Inhibition |
|---|---|---|
| NL2 | 0.01% | 0.9 |
| NL2 | 0.1% | 0.79 |
| NL2 | 1.0% | 0.68 |
| NL6 | 0.01% | 0.48 |
| NL6 | 0.1% | 0.5 |
| NL6 | 1.0% | 0.64 |
| NL6 | 0.01% | 1.19 |
| NL6 | 0.1% | 1.19 |
| NL6 | 1.0% | 0.6 |

EXAMPLE 10

Induction of Endothelial Cell Apoptosis

The ability of the NL2, NL3 and NL6 to induce apoptosis in endothelial cells was tested in human venous umbilical vein endothelial cells (HUVEC, Cell Systems), using a 96-well format, in 0% serum medium supplemented with 100 ng/ml VEGF. (As HUVEC cells are easily dislodged from the plating surface, all pipetting in the wells must be done as gently as practicable.)

The medium was aspired and the cells washed once with PBS. 5 ml of 1×trypsin was added to the cells in a T-175 flask, and the cells were allowed to stand until they were released from the plate (about 5–10 minutes). Trypsinization was stopped by adding 5 ml of growth media. The cells were spun at 1000 rpm for 5 minutes at 4 ° C. The medium was aspirated and the cells were resuspended in 10 ml of 10% serum complemented medium (Cell Systems), 1×penn/strep.

The cells were plated on 96-well microtiterplates (Amersham Life Science, cytostar-T scintillating microplate, RPNQ160, sterile, tissue-culture treated, individually wrapped), in 10% serum (CSG-medium, Cell Systems), at a density of $2 \times 10^4$ cells per well in a total volume of 100 μl. The NL5 and NL8 polypeptides were added in triplicate at dilutions of 1%, 0.33% and 0.11%. Wells without cells were used as a blank and wells with cells only as a negative control. As a positive control 1:3 serial dilutions of 50μl of a 3×stock of staurosporine were used. The ability of the NL5 polypeptide to induce apoptosis was determined using Annexin V, a member of the calcium and phospholipid binding proteins, to detect apoptosis.

0.2 ml Annexin V—Biotin stock solution (100μg/ml) were diluted in 4.6 ml 2×Ca$^{2+}$ binding buffer and 2.5% BSA (1:25 dilution). 50 μls of the dilutedAnnexin V—Biotin solution were added to each well (except controls) to a final concentration of 1.0 μg/ml. The samples were incubated for 10–15 minutes with Annexin-Biotin prior to direct addition of $^{35}$S-Streptavidin. $^{35}$S-Streptavidin was diluted in $2\times Ca^{2+}$ Binding buffer, 2.5% BSA and was added to all wells at a final concentration of $3\times 10^4$ cpm/well. The plates were then sealed, centrifuged at 1000 rpm for 15 minutes and placed on orbital shaker for 2 hours. The analysis was performed on 1450 Microbeta Trilux (Wallac).

NL2, NL3 and NL6 were positive in this assay. This result further confirms the potential utility of these, and potentially related, molecules in cancer therapy.

EXAMPLE 11

Induction of c-fos in endothelial cells

Human venous umbilical vein endothelial cells (HUVEC, Cell Systems) in growth media (50% Ham's F12 w/o GHT: low glucose, and 50% DMEM without glycine: with $NaHCO_3$, 1% glutamine, 10 mM Hepes, 10% FBS, 10 ng/ml bFGF), were plated on 96-well microtiter plates at a cell density of $1\times 10^4$ cells/well. The day after plating, the cells were starved by removing the growth media and treating the cells with 100 μl/well test samples and controls (positive control: growth media; negative control: 10 mM HEPES, 140 mM NaCl, 4% (w/v) mannitol, pH 6.8). The cells were incubated for 30 minutes at 37° C., in 5% $CO_2$. The samples were removed, and the first part of the bDNA kit protocol (Chiron Diagnostics, cat. #6005-037) was followed, where each capitalized reagent/buffer listed below was available from the kit.

Briefly, the amounts of the TM Lysis Buffer and Probes needed for the tests were calculated based on information provided by the manufacturer. The appropriate amounts of thawed Probes were added to the TM Lysis Buffer. The Capture Hybridization Buffer was warmed to room temperature. The bDNA strips were set up in the metal strip holders, and 100 μl of Capture Hybridization Buffer were added to each b-DNA well needed, followed by incubation for at least 30 minutes. The test plates with the cells were removed from the incubator, and the medium was gently removed using the vacuum manifold. 100 μl of Lysis Hybridization Buffer with Probes were quickly pipetted into each well of the microtiter plates. The plates were then incubated at 55° C. for 15 minutes. Upon removal from the incubator, the plates were placed on the vortex mixer with the microtiter adapter head and vortex on the #2 setting for one minute. 80 μl of the lysate were removed and added to the bDNA wells containing the Capture Hybridization Buffer, and pipetted up and down to mix. The plates were incubated at 53° C. for at least 16 hours.

On the next day, the second part of the bDNA kit protocol was followed. Specifically, the Plates were removed from the incubator and placed on the bench to cool for 10 minutes. The volumes of additions needed were calculated based upon information provided by the manufacturer. An Amplifier Working Solution was prepared by making a 1:100 dilution of the Amplifier Concentrate (20 fm/μl) in AL Hybridization Buffer. The hybridization mixture was removed from the plates and washed twice with Wash A. 50 μl of Amplifier Working Solution were added to each well and the wells were incubated at 53° C. for 30 minutes. The plates were then removed from the incubator and allowed to cool for 10 minutes. The Label Probe Working Solution was prepared by making a 1:100 dilution of Label Concentrate (40 pmoles/μl) in AL Hybridization Buffer. After the 10 minutes cool down period, the Amplifier Hybridization Mixture was removed and the plates washed twice with Wash A. 50 μl of Label Probe Working Solution were added to each well and the wells were incubated at 53° C. for 15 minutes. After cooling for 10 minutes, the Substrate was warmed to room temperature. Upon addition of 3 μl of Substrate Enhancer to each ml of Substrate needed for the assay, the plates were allowed to cool for 10 minutes, the Label Hybridization Mixture was removed, and the plates were washed twice with Wash A and three-times with Wash D. 50 μl of the Substrate Solution with Enhancer were added to each well. The plates were incubated for 30 minutes at 37° C. and RLU read in an appropriate luminometer.

The replicates were averaged and the coefficient of variation was determined. The measure of activity of the fold increase over the negative control (HEPES buffer described above) value was indicated by chemoluminescence units (RLU). Samples which showed an at least two-fold value over the negative control value were considered positive.

TABLE 2

| Protein Name | Protein Concentration | Relative Activity |
| --- | --- | --- |
| NL6 | 0.1% | 1.23 |
| NL6 | 1.0% | 1.69 |
| NL6 | 10.0% | 2.43 |

EXAMPLE 12

Endothelial Cell Ca Influx Assay

Ca influx is a well documented response upon binding of certain ligands to their receptors. A test compound that results in a positive response in the present Ca influx assay can be said to bind to a specific receptor and activate a biological signalling pathway in human endothelial cells. This could ultimately lead, for example, to cell division, inhibition of cell proliferation, endothelial tube formation, cell migration, apoptosis, etc.

Human venous umbilical vein endothelial cells (HUVEC, Cell Systems) in growth media (50:50 without glycine, 1% glutamine, 10 mM Hepes, 10% FBS, 10 ng/mi bFGF), were plated on 96-well Viewplates-96 (Packard Instrument Company Part #6005182) microtiter plates at a cell density of $2\times 10^4$ cells/well. The cells were washed with buffer (HBSS+ 10 mM Hepes) three-times, leaving 100 μl per well. Test samples of the NL6 polypeptide were prepared on a different 96-well plate at 5×concentration in buffer. Positive control: 50 μM ionomycin (5x); negative control: Protein 32. The Cell plate and sample plates were run on an FLIPR (Molecular Devices) machine. The FLIPR machine added 25 μl of test sample to the cells, and the readings were taken every second for one minute, then every 3 seconds for the next 3 minutes.

TABLE 3

| Protein Name | Protein Concentration | Relative Activity |
| --- | --- | --- |
| NL6 | 0.01% | 1.0 |
| NL6 | 0.01% | 1.0 |
| NL6 | 1.0% | 3.0 |
| NL6 | 0.01% | 1.0 |
| NL6 | 0.1% | 1.0 |
| NL6 | 1.0% | 3.0 |

Hairless guinea pigs weighing 350 grams or more were anesthetized with ketamine (75–80 mg/kg) and xylazine (5 mg/kg) intramuscularly. NL6 or conditioned medium test samples were injected intradermally onto the backs with 100 μl per injection site. There were approximately 16–24 injection sites per animal. One ml of Evans blue dye (1% in physiologic buffered saline) was injected intracardially. Proinflammatory or skin vascular permeability responses to the test compound were scored visually, by measuring the diameter of blue color leaked from the site of injection at 1 and 6 hours post administration of the test material (NL6). The animals were sacrificed 6 hours after administration. Each skin site was biopsied and fixed in formalin. The skins were prepared for histopathologic evaluation. Each site was evaluated for inflammatory cell infiltration into the skin. Sites with visible inflammatory cell infiltration were scored as positive. Inflammatory cells infiltrates can be neutrophilic, eosinophlic, monocytic, or lymphocytic. NL6 was identified as a potential proinflammatory substance in this assay.

EXAMPLE 14

Stimulation of Endothelial Tube Formation

This assay follows the assay described in Davis and Camarillo, *Experimental Cell Research,* 24:39–51 (1996), or one modified from it as follows:

Protocol: HUVE cells (passage number less than 8 from primary) are mixed with type I rat tail collagen, final concentration 2.6 mg/ml at a density of $6 \times 10^5$ cells/ml and plated at 50 μl per well on a 96-well plate. The gel is allowed to solidify for 1 hr at 37° C., then 50 μl per well of M199 culture media supplemented with 1% FBS and an NL6 polypeptide sample (at dilutions of 1%, 0.1%, and 0.01%, respectively) is added along with 1 μM 6-FAM-FITC dye to stain vacuoles while they are forming. Cells are incubated at 37° C./5% $CO_2$ for 48 hr, fixed with 3.7% formalin at room temperature for 10 minutes, washed with PBS five times, then stained with Rh-Phalloidin at 4° C. overnight followed by nuclear staining with 4 μM DAPI.

1. Apoptosis Assay

This assay will identify factors that facilitate cell survival in a 3-dimensional matrix in the presence of exogenous growth factors (VEGF, bFGF without PMA).

A positive result is equal to or less than 1.0=no apoptosis, 1=less than 20% cells are apoptotic, 2=less than 50% cells are apoptotic, 3=greater than 50% cells are apoptotic. Stimulators of apoptosis in this system are expected to be apoptotic factors, and inhibitors are expected to prevent or lessen apoptosis.

2. Vacuoles Assay

This assay will identify factors that stimulate endothelial vacuole formation and lumen formation in the presence of bFGF and VEGF (40 ng/ml).

A positive result is equal to or greater than 2. 1=vacuoles present in less than 20% of cells, 2=vacuoles present in 20–50% of cells, 3=vacuoles present in greater than 50% of cells. This assay is designed to identify factors that are involved in stimulating pinocytosis, ion pumping, permeability, and junction formation.

3. Tube Formation Assay

This assay is to identify factors that stimulate endothelial tube formation in a 3-dimensional matrix. This assay will identify factors that stimulate endothelial cells to differentiate into a tube-like structure in a 3-dimensional matrix in the presence of exogenous growth factors (VEGF, bFGF).

A positive result is equal to or greater than 2. 1=cells are all round, 2=cells are elongated, 3=cells are forming tubes with some connections, 4=cells are forming complex tubular networks. This assay would identify factors that may be involved in stimulating tracking chemotaxis, or endothelial shape change.

Figure 10:
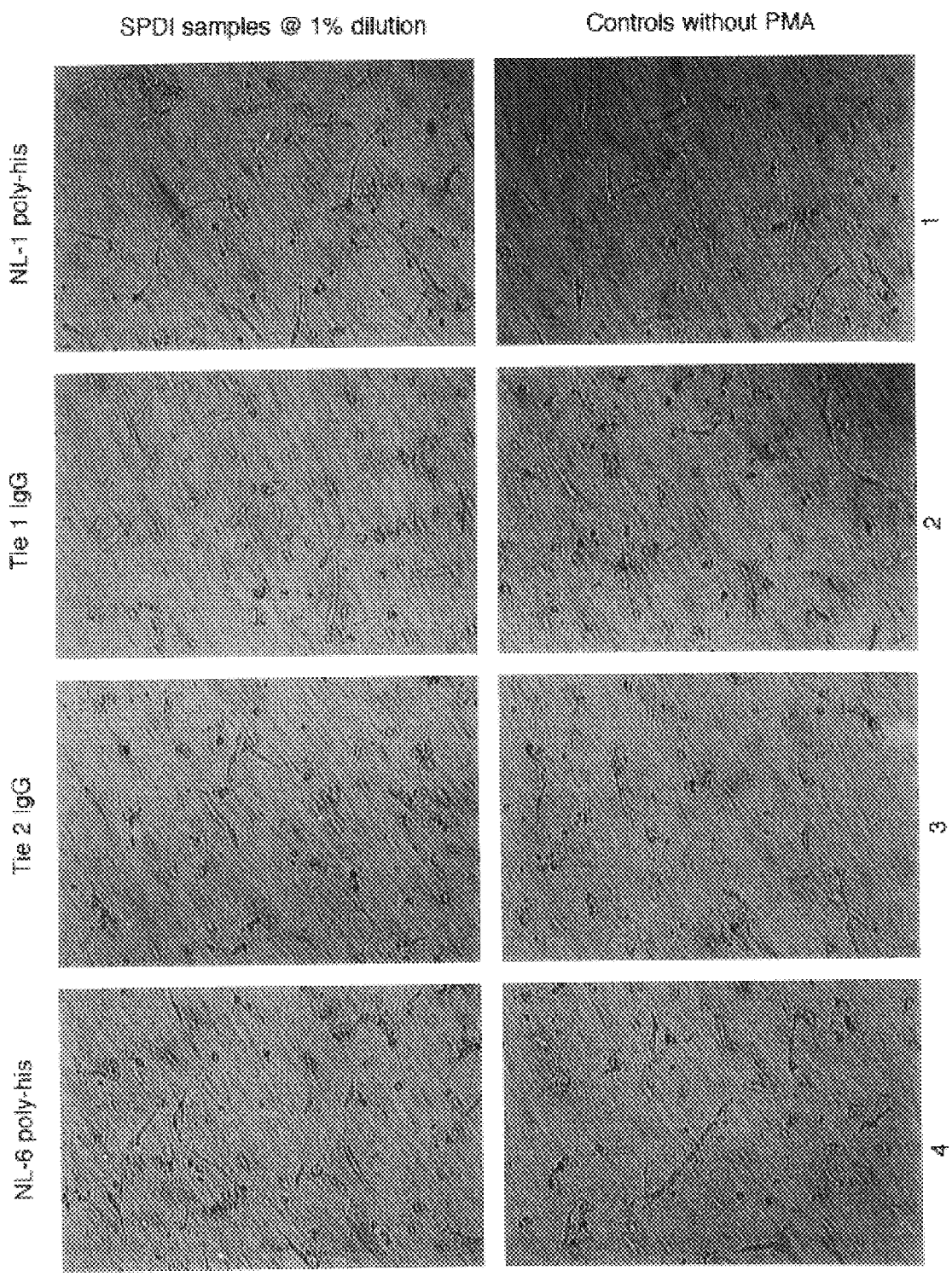
FIG. 10 shows the effect on HUVEC tube formation of the NL6 polypeptide conjugated to poly-his at 1% dilution and of a buffer control (10 mM HEPES/0.14M NaCl/4% mannitol, pH 6.8) at 1% dilution. Comparative results with another novel TIE ligand homologue (NL1) and two known TIE ligands TIE-1 and TIE-2, tested as IgG fusions, are also shown in the Figure.

FIG. 10 shows the effect on HUVEC tube formation of the NL6 polypeptide conjugated to poly-his at 1% dilution and of a buffer control (10 mM HEPES/0.14M NaCl/4% mannitol, pH 6.8) at 1% dilution. Comparative results with another novel TIE ligand homologue (NL1) and two known TIE ligands TIE-1 and TIE-2, tested as IgG fusions, are also shown in the FIG. 10.

Deposit of Material

As noted before, the following materials have been deposited with the American Type Culture Collection, 10801 University Boulevard, Manassas Va. 20110-2209, USA (ATCC):

| Material | ATCC Dep. No. | Deposit Date |
|---|---|---|
| NL2-DNA 22780-1078 | 209284 | 9/18/97 |
| NL3-DNA 33457-1078 | 209283 | 9/18/97 |
| FLS139-DNA 16451-1078 | 209281 | 9/18/97 |

These deposits were made under the provisions of the Budapest Treaty on the International cognition of the Deposit of Microorganisms for the Purpose of Patent Procedure and the Regulations thereunder (Budapest Treaty). This assures maintenance of a viable culture of the deposit for 30 years from the date of the deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the rtinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and Commissioner's rules pursuant thereto (including 37 C.F.R. §1.14 with particular reference to 886 OG 683).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The present specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of the invention. The deposit of material herein does not constitute an admission that the written description is inadequate to enable the practice of any aspect of the invention, including the best more thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated nucleic acid molecule encoding a TIE ligand homologue polypeptide having at least 90% sequence identity with the human NL6 ligand of SEQ ID NO:6, and being capable of inducing apoptosis or causing tube formation in human venous umbilical vein endothelial cells (HUVE cells).

2. The isolated nucleic acid molecule of claim 1 which comprises the fibrinogen-like domain of SEQ ID NO: 5.

3. A vector which comprises said nucleic acid molecule of claim 1.

4. A recombinant host cell transformed with said nucleic acid molecule according to claim 1.

5. The recombinant host cell of claim 4 which is a prokaryotic cell.

6. The recombinant host cell of claim 4 which is a eukaryotic cell.

7. An isolated mammalian TIE ligand homologue polypeptide having at least 90% sequence identity with the human NL6 ligand of SEQ ID NO:6, and being capable of inducing apoptosis or causing tube formation in human venous umbilical vein endothelial cells (HUVE cells).

8. A composition comprising said polypeptide of claim 7 in association with a carrier.

9. A conjugate comprising said polypeptide of claim 7 fused to a therapeutic or cytotoxic agent.

10. The conjugate of claim 9 wherein said therapeutic agent is a toxin, a TIE ligand, or a member of the vascular endothelial growth factor (VEGF) family.

* * * * *

SEQUENCE LISTING

<160> NUMBER OF SEQ ID NOS: 17

<210> SEQ ID NO 1
<211> LENGTH: 1869
<212> TYPE: DNA
<213> ORGANISM: Homo sapiens

<400> SEQUENCE: 1

| | | | | | |
|---|---|---|---|---|---|
| gccgagctga | gcggatcctc | acatgactgt | gatccgattc | tttccagcgg | 50 |
| cttctgcaac | caagcgggtc | ttaccccgg | tcctccgcgt | ctccagtcct | 100 |
| cgcacctgga | accccaacgt | ccccgagagt | ccccgaatcc | ccgctcccag | 150 |
| gctacctaag | aggatgagcg | gtgctccgac | ggccggggca | gccctgatgc | 200 |
| tctgcgccgc | caccgccgtg | ctactgagcg | ctcaggggg | accgtgcag | 250 |
| tccaagtcgc | cgcgctttgc | gtcctgggac | gagatgaatg | tcctggcgca | 300 |
| cggactcctg | cagctcggcc | aggggctgcg | cgaacacgcg | gagcgcaccc | 350 |
| gcagtcagct | gagcgcgctg | gagcggcgcc | tgagcgcgtg | cgggtccgcc | 400 |
| tgtcagggaa | ccgaggggtc | caccgacctc | ccgttagccc | ctgagagccg | 450 |
| ggtggaccct | gaggtccttc | acagcctgca | gacacaactc | aaggctcaga | 500 |
| acagcaggat | ccagcaactc | ttccacaagg | tgcccagca | gcagcggcac | 550 |
| ctggagaagc | agcacctgcg | aattcagcat | ctgcaaagca | gtttggcct | 600 |
| cctggaccac | aagcacctag | accatgaggt | ggccaagcct | gcccgaagaa | 650 |
| agaggctgcc | cgagatggcc | cagccagttg | acccggctca | caatgtcagc | 700 |
| cgcctgcacc | ggctgcccag | ggattgccag | gagctgttcc | aggttgggga | 750 |
| gaggcagagt | ggactatttg | aaatccagcc | tcaggggtct | ccgccatttt | 800 |
| tggtgaactg | caagatgacc | tcagatggag | gctggacagt | aattcagagg | 850 |
| cgccacgatg | gctcagtgga | cttcaaccgg | ccctgggaag | cctacaaggc | 900 |
| ggggtttggg | gatccccacg | gcgagttctg | gctgggtctg | gagaaggtgc | 950 |
| atagcatcac | ggggaccgc | aacagccgcc | tggccgtgca | gctgcgggac | 1000 |
| tgggatggca | acgccgagtt | gctgcagttc | tccgtgcacc | tgggtggcga | 1050 |
| ggacacggcc | tatagcctgc | agctcactgc | acccgtggcc | ggccagctgg | 1100 |
| gcgccaccac | cgtcccaccc | agcggcctct | ccgtaccctt | ctccacttgg | 1150 |
| gaccaggatc | acgacctccg | cagggacaag | aactgcgcca | agagcctctc | 1200 |
| tggaggctgg | tggtttggca | cctgcagcca | ttccaacctc | aacggccagt | 1250 |
| acttccgctc | catcccacag | cagcggcaga | agcttaagaa | gggaatcttc | 1300 |
| tggaagacct | ggcggggccg | ctactacccg | ctgcaggcca | ccaccatgtt | 1350 |
| gatccagccc | atggcagcag | aggcagcctc | ctagcgtcct | ggctgggcct | 1400 |
| ggtcccaggc | ccacgaaaga | cggtgactct | ggctctgcc | cgaggatgtg | 1450 |
| gccgttccct | gcctgggcag | gggctccaag | gagggccat | ctggaaactt | 1500 |
| gtggacagag | aagaagacca | cgactggaga | agccccttt | ctgagtgcag | 1550 |
| gggggctgca | tgcgttgcct | cctgagatcg | aggctgcagg | atatgctcag | 1600 |
| actctagagg | cgtggaccaa | ggggcatgga | gcttcactcc | ttgctggcca | 1650 |
| gggagttggg | gactcagagg | gaccacttgg | ggccagccag | actggcctca | 1700 |

```
atggcggact cagtcacatt gactgacggg gaccagggct tgtgtgggtc              1750
gagagcgccc tcatggtgct ggtgctgttg tgtgtaggtc ccctggggac              1800
acaagcaggc gccaatggta tctgggcgga gctcacagag ttcttggaat              1850
aaaagcaacc tcagaacac                                                1869
```

<210> SEQ ID NO 2
<211> LENGTH: 406
<212> TYPE: PRT
<213> ORGANISM: Homo sapiens
<220> FEATURE:
<221> NAME/KEY: unsure
<222> LOCATION: 221
<223> OTHER INFORMATION: unknown amino acid

<400> SEQUENCE: 2

```
Met Ser Gly Ala Pro Thr Ala Gly Ala Leu Met Leu Cys Ala
  1               5                  10                  15

Ala Thr Ala Val Leu Leu Ser Ala Gln Gly Gly Pro Val Gln Ser
                 20                  25                  30

Lys Ser Pro Arg Phe Ala Ser Trp Asp Glu Met Asn Val Leu Ala
                 35                  40                  45

His Gly Leu Leu Gln Leu Gly Gln Gly Leu Arg Glu His Ala Glu
                 50                  55                  60

Arg Thr Arg Ser Gln Leu Ser Ala Leu Glu Arg Arg Leu Ser Ala
                 65                  70                  75

Cys Gly Ser Ala Cys Gln Gly Thr Glu Gly Ser Thr Asp Leu Pro
                 80                  85                  90

Leu Ala Pro Glu Ser Arg Val Asp Pro Glu Val Leu His Ser Leu
                 95                 100                 105

Gln Thr Gln Leu Lys Ala Gln Asn Ser Arg Ile Gln Gln Leu Phe
                110                 115                 120

His Lys Val Ala Gln Gln Gln Arg His Leu Glu Lys Gln His Leu
                125                 130                 135

Arg Ile Gln His Leu Gln Ser Gln Phe Gly Leu Leu Asp His Lys
                140                 145                 150

His Leu Asp His Glu Val Ala Lys Pro Ala Arg Arg Lys Arg Leu
                155                 160                 165

Pro Glu Met Ala Gln Pro Val Asp Pro Ala His Asn Val Ser Arg
                170                 175                 180

Leu His Arg Leu Pro Arg Asp Cys Gln Glu Leu Phe Gln Val Gly
                185                 190                 195

Glu Arg Gln Ser Gly Leu Phe Glu Ile Gln Pro Gln Gly Ser Pro
                200                 205                 210

Pro Phe Leu Val Asn Cys Lys Met Thr Ser Xaa Gly Gly Trp Thr
                215                 220                 225

Val Ile Gln Arg Arg His Asp Gly Ser Val Asp Phe Asn Arg Pro
                230                 235                 240

Trp Glu Ala Tyr Lys Ala Gly Phe Gly Asp Pro His Gly Glu Phe
                245                 250                 255

Trp Leu Gly Leu Glu Lys Val His Ser Ile Thr Gly Asp Arg Asn
                260                 265                 270

Ser Arg Leu Ala Val Gln Leu Arg Asp Trp Asp Gly Asn Ala Glu
                275                 280                 285

Leu Leu Gln Phe Ser Val His Leu Gly Gly Glu Asp Thr Ala Tyr
```

```
                    290                 295                 300
            Ser Leu Gln Leu Thr Ala Pro Val Ala Gly Gln Leu Gly Ala Thr
                            305                 310                 315
            Thr Val Pro Pro Ser Gly Leu Ser Val Pro Phe Ser Thr Trp Asp
                            320                 325                 330
            Gln Asp His Asn Leu Arg Arg Asp Lys Asn Cys Ala Lys Ser Leu
                            335                 340                 345
            Ser Gly Gly Trp Trp Phe Gly Thr Cys Ser His Ser Asn Leu Asn
                            350                 355                 360
            Gly Gln Tyr Phe Arg Ser Ile Pro Gln Gln Arg Gln Lys Leu Lys
                            365                 370                 375
            Lys Gly Ile Phe Trp Lys Thr Trp Arg Gly Arg Tyr Tyr Pro Leu
                            380                 385                 390
            Gln Ala Thr Thr Met Leu Ile Gln Pro Met Ala Ala Glu Ala Ala
                            395                 400                 405
            Ser

<210> SEQ ID NO 3
<211> LENGTH: 1024
<212> TYPE: DNA
<213> ORGANISM: Homo sapiens

<400> SEQUENCE: 3
cggacgcgtg ggcccctggt gggcccagca agatggatct actgtggatc                50
ctgccctccc tgtggcttct cctgcttggg gggcctgcct gcctgaagac               100
ccaggaacac cccagctgcc caggacccag ggaactggaa gccagcaaag               150
ttgtcctcct gcccagttgt cccggagctc aggaagtcc tggggagaag                200 ggagccccag gtcctcaagg ccacctggac caccaggca agatgggccc                250 caagggtgag ccaggcccca gaaactgccg ggagctgttg agccagggcg               300
ccaccttgag cggctggtac catctgtgcc tacctgaggg cagggccctc               350
ccagtctttt gtgacatgga caccgagggg ggcggctggc tggtgtttca               400
gaggcgccag gatggttctg tggatttctt ccgctcttgg tcctcctaca               450
gagcaggttt tgggaaccaa gagtctgaat tctggctggg aaatgagaat               500
ttgcaccagc ttactctcca gggtaactgg gagctgcggg tagagctgga               550
agactttaat ggtaaccgta ctttcgccca ctatgcgacc ttccgcctcc               600
tcggtgaggt agaccactac cagctggcac tgggcaagtt ctcagagggc               650
actgcagggg attccctgag cctccacagt gggaggccct ttaccaccta               700
tgacgctgac cacgattcaa gcaacagcaa ctgtgcagtg attgtccacg               750
gtgcctggtg gtatgcatcc tgttaccgat caaatctcaa tggtcgctat               800
gcagtgtctg aggctgccgc ccacaaatat ggcattgact gggcctcagg               850
ccgtggtgtg ggccacccct accgcagggt tcggatgatg cttcgatagg               900
gcactctggc agccagtgcc cttatctctc ctgtacagct tccggatcgt               950
cagccacctt gcctttgcca accacctctg cttgcctgtc cacatttaaa              1000
aataaaatca ttttagccct ttca                                          1024

<210> SEQ ID NO 4
<211> LENGTH: 288
<212> TYPE: PRT
```

<213> ORGANISM: Homo sapiens

<400> SEQUENCE: 4

```
Met Asp Leu Leu Trp Ile Leu Pro Ser Leu Trp Leu Leu Leu
 1               5                  10                  15

Gly Gly Pro Ala Cys Leu Lys Thr Gln Glu His Pro Ser Cys Pro
             20                  25                  30

Gly Pro Arg Glu Leu Glu Ala Ser Lys Val Val Leu Leu Pro Ser
             35                  40                  45

Cys Pro Gly Ala Pro Gly Ser Pro Gly Glu Lys Gly Ala Pro Gly
             50                  55                  60

Pro Gln Gly Pro Pro Gly Pro Pro Gly Lys Met Gly Pro Lys Gly
             65                  70                  75

Glu Pro Gly Pro Arg Asn Cys Arg Glu Leu Leu Ser Gln Gly Ala
             80                  85                  90

Thr Leu Ser Gly Trp Tyr His Leu Cys Leu Pro Glu Gly Arg Ala
             95                  100                 105

Leu Pro Val Phe Cys Asp Met Asp Thr Glu Gly Gly Gly Trp Leu
             110                 115                 120

Val Phe Gln Arg Arg Gln Asp Gly Ser Val Asp Phe Phe Arg Ser
             125                 130                 135

Trp Ser Ser Tyr Arg Ala Gly Phe Gly Asn Gln Glu Ser Glu Phe
             140                 145                 150

Trp Leu Gly Asn Glu Asn Leu His Gln Leu Thr Leu Gln Gly Asn
             155                 160                 165

Trp Glu Leu Arg Val Glu Leu Glu Asp Phe Asn Gly Asn Arg Thr
             170                 175                 180

Phe Ala His Tyr Ala Thr Phe Arg Leu Leu Gly Glu Val Asp His
             185                 190                 195

Tyr Gln Leu Ala Leu Gly Lys Phe Ser Glu Gly Thr Ala Gly Asp
             200                 205                 210

Ser Leu Ser Leu His Ser Gly Arg Pro Phe Thr Thr Tyr Asp Ala
             215                 220                 225

Asp His Asp Ser Ser Asn Ser Asn Cys Ala Val Ile Val His Gly
             230                 235                 240

Ala Trp Trp Tyr Ala Ser Cys Tyr Arg Ser Asn Leu Asn Gly Arg
             245                 250                 255

Tyr Ala Val Ser Glu Ala Ala His Lys Tyr Gly Ile Asp Trp
             260                 265                 270

Ala Ser Gly Arg Gly Val Gly His Pro Tyr Arg Arg Val Arg Met
             275                 280                 285

Met Leu Arg
```

<210> SEQ ID NO 5
<211> LENGTH: 2042
<212> TYPE: DNA
<213> ORGANISM: Homo sapiens

<400> SEQUENCE: 5

| | |
|---|---|
| gcggacgcgt gggtgaaatt gaaaatcaag ataaaaatgt tcacaattaa | 50 |
| gctccttctt tttattgttc ctctagttat ttcctccaga attgatcaag | 100 |
| acaattcatc atttgattct ctatctccag agccaaaatc aagatttgct | 150 |
| atgttagacg atgtaaaaat tttagccaat ggcctccttc agttgggaca | 200 |

```
tggtcttaaa gactttgtcc ataagacgaa gggccaaatt aatgacatat         250
ttcaaaaact caacatattt gatcagtctt tttatgatct atcgctgcaa         300
accagtgaaa tcaaagaaga agaaaaggaa ctgagaagaa ctacatataa         350
actacaagtc aaaaatgaag aggtaaagaa tatgtcactt gaactcaact         400
caaaacttga agcctccta gaagaaaaaa ttctacttca acaaaagtg          450 aaatatttag aagagcaact aactaactta attcaaaatc aacctgaaac         500
tccagaacac ccagaagtaa cttcacttaa aacttttgta gaaaaacaag        550
ataatagcat caaagacctt ctccagaccg tggaagacca atataaacaa        600
ttaaaccaac agcatagtca aataaaagaa atagaaaatc agctcagaag        650
gactagtatt caagaaccca cagaaatttc tctatcttcc aagccaagag        700
caccaagaac tactccctttt cttcagttga atgaaataag aaatgtaaaa       750
catgatggca ttcctgctga atgtaccacc atttataaca gaggtgaaca        800
tacaagtggc atgtatgcca tcagacccag caactctcaa gttttttcatg       850 tctactgtga tgttatatca ggtagtccat ggacattaat tcaacatcga        900
atagatggat cacaaaactt caatgaaacg tgggagaact acaaatatgg        950
ttttgggagg cttgatggag aattttggtt gggcctagag aagatatact       1000
ccatagtgaa gcaatctaat tatgttttac gaattgagtt ggaagactgg        1050
aaagacaaca aacattatat tgaatattct ttttacttgg gaaatcacga        1100
aaccaactat acgctacatc tagttgcgat tactggcaat gtccccaatg        1150
caatcccgga aaacaaagat ttggtgtttt ctacttggga tcacaaagca        1200
aaaggacact tcaactgtcc agagggttat tcaggaggct ggtggtggca        1250
tgatgagtgt ggagaaaaca acctaaatgg taaatataac aaaccaagag        1300
caaaatctaa gccagagagg agaagaggat tatcttggaa gtctcaaaat        1350
ggaaggttat actctataaa atcaaccaaa atgttgatcc atccaacaga        1400
ttcagaaagc tttgaatgaa ctgaggcaat taaaggcat attttaaccat        1450 taactcattc caagttaatg tggtctaata atctggtata aatccttaag        1500
agaaagcttg agaaatagat tttttttatc ttaaagtcac tgtctatta         1550 agattaaaca tacaatcaca taaccttaaa gaataccgtt tacatttctc         1600
aatcaaaatt cttataatac tatttgtttt aaattttgtg atgtgggaat        1650
caattttaga tggtcacaat ctagattata atcaataggt gaacttatta        1700 aataacttt ctaaataaaa aatttagaga cttttatttt aaaaggcatc          1750
atatgagcta atatcacaac tttcccagtt taaaaaacta gtactcttgt        1800
taaaactcta aacttgacta aatacagagg actggtaatt gtacagttct        1850
taaatgttgt agtattaatt tcaaaactaa aaatcgtcag cacagagtat        1900
gtgtaaaaat ctgtaataca aatttttaaa ctgatgcttc attttgctac         1950
aaaataattt ggagtaaatg tttgatatga tttatttatg aaacctaatg        2000
aagcagaatt aaatactgta ttaaaataag ttcgctgtct tt                2042

<210> SEQ ID NO 6
<211> LENGTH: 460
<212> TYPE: PRT
<213> ORGANISM: Homo sapiens
```

<400> SEQUENCE: 6

```
Met Phe Thr Ile Lys Leu Leu Phe Ile Val Pro Leu Val Ile
  1               5                  10                  15

Ser Ser Arg Ile Asp Gln Asp Asn Ser Phe Asp Ser Leu Ser
                 20                  25                  30

Pro Glu Pro Lys Ser Arg Phe Ala Met Leu Asp Asp Val Lys Ile
                 35                  40                  45

Leu Ala Asn Gly Leu Leu Gln Leu Gly His Gly Leu Lys Asp Phe
                 50                  55                  60

Val His Lys Thr Lys Gly Gln Ile Asn Asp Ile Phe Gln Lys Leu
                 65                  70                  75

Asn Ile Phe Asp Gln Ser Phe Tyr Asp Leu Ser Leu Gln Thr Ser
                 80                  85                  90

Glu Ile Lys Glu Glu Glu Lys Glu Leu Arg Arg Thr Thr Tyr Lys
                 95                 100                 105

Leu Gln Val Lys Asn Glu Glu Val Lys Asn Met Ser Leu Glu Leu
                110                 115                 120

Asn Ser Lys Leu Glu Ser Leu Leu Glu Glu Lys Ile Leu Leu Gln
                125                 130                 135

Gln Lys Val Lys Tyr Leu Glu Glu Gln Leu Thr Asn Leu Ile Gln
                140                 145                 150

Asn Gln Pro Glu Thr Pro Glu His Pro Glu Val Thr Ser Leu Lys
                155                 160                 165

Thr Phe Val Glu Lys Gln Asp Asn Ser Ile Lys Asp Leu Leu Gln
                170                 175                 180

Thr Val Glu Asp Gln Tyr Lys Gln Leu Asn Gln Gln His Ser Gln
                185                 190                 195

Ile Lys Glu Ile Glu Asn Gln Leu Arg Arg Thr Ser Ile Gln Glu
                200                 205                 210

Pro Thr Glu Ile Ser Leu Ser Ser Lys Pro Arg Ala Pro Arg Thr
                215                 220                 225

Thr Pro Phe Leu Gln Leu Asn Glu Ile Arg Asn Val Lys His Asp
                230                 235                 240

Gly Ile Pro Ala Glu Cys Thr Thr Ile Tyr Asn Arg Gly Glu His
                245                 250                 255

Thr Ser Gly Met Tyr Ala Ile Arg Pro Ser Asn Ser Gln Val Phe
                260                 265                 270

His Val Tyr Cys Asp Val Ile Ser Gly Ser Pro Trp Thr Leu Ile
                275                 280                 285

Gln His Arg Ile Asp Gly Ser Gln Asn Phe Asn Glu Thr Trp Glu
                290                 295                 300

Asn Tyr Lys Tyr Gly Phe Gly Arg Leu Asp Gly Glu Phe Trp Leu
                305                 310                 315

Gly Leu Glu Lys Ile Tyr Ser Ile Val Lys Gln Ser Asn Tyr Val
                320                 325                 330

Leu Arg Ile Glu Leu Glu Asp Trp Lys Asp Asn Lys His Tyr Ile
                335                 340                 345

Glu Tyr Ser Phe Tyr Leu Gly Asn His Glu Thr Asn Tyr Thr Leu
                350                 355                 360

His Leu Val Ala Ile Thr Gly Asn Val Pro Asn Ala Ile Pro Glu
                365                 370                 375

Asn Lys Asp Leu Val Phe Ser Thr Trp Asp His Lys Ala Lys Gly
```

```
                380             385              390
    His Phe Asn Cys Pro Glu Gly Tyr Ser Gly Gly Trp Trp His
                    395             400              405
    Asp Glu Cys Gly Glu Asn Asn Leu Asn Gly Lys Tyr Asn Lys Pro
                        410             415              420
    Arg Ala Lys Ser Lys Pro Glu Arg Arg Arg Gly Leu Ser Trp Lys
                        425             430              435
    Ser Gln Asn Gly Arg Leu Tyr Ser Ile Lys Ser Thr Lys Met Leu
                        440             445              450
    Ile His Pro Thr Asp Ser Glu Ser Phe Glu
                    455             460
```

```
<210> SEQ ID NO 7
<211> LENGTH: 33
<212> TYPE: DNA
<213> ORGANISM: Artificial Sequence
<220> FEATURE:
<223> OTHER INFORMATION: Synthetic oligonucleotide probe

<400> SEQUENCE: 7
atgaggtggc caagcctgcc cgaagaaaga ggc                              33

<210> SEQ ID NO 8
<211> LENGTH: 39
<212> TYPE: DNA
<213> ORGANISM: Artificial Sequence
<220> FEATURE:
<223> OTHER INFORMATION: Synthetic oligonucleotide probe

<400> SEQUENCE: 8
caactggctg ggccatctcg ggcagcctct ttcttcggg                        39

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 9
cccagccaga actcgccgtg ggga                                        24

<210> SEQ ID NO 10
<211> LENGTH: 33
<212> TYPE: DNA
<213> ORGANISM: Artificial Sequence
<220> FEATURE:
<223> OTHER INFORMATION: Synthetic oligonucleotide probe

<400> SEQUENCE: 10
tggttggcaa aggcaaggtg gctgacgatc cgg                              33

<210> SEQ ID NO 11
<211> LENGTH: 43
<212> TYPE: DNA
<213> ORGANISM: Artificial Sequence
<220> FEATURE:
<223> OTHER INFORMATION: Synthetic oligonucleotide probe

<400> SEQUENCE: 11
gtggccctta tctctcctgt acagcttccg gatcgtcagc cac                   43

<210> SEQ ID NO 12
```

```
<211> LENGTH: 27
<212> TYPE: DNA
<213> ORGANISM: Artificial Sequence
<220> FEATURE:
<223> OTHER INFORMATION: Synthetic oligonucleotide probe

<400> SEQUENCE: 12
tccattccca cctatgacgc tgaccca                                              27

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 13
ccacgttggc ttgaaattga                                                     20

<210> SEQ ID NO 14
<211> LENGTH: 50
<212> TYPE: DNA
<213> ORGANISM: Artificial Sequence
<220> FEATURE:
<223> OTHER INFORMATION: Synthetic oligonucleotide probe

<400> SEQUENCE: 14
cctccagaat tgatcaagac aattcatgat ttgattctct atctccagag                    50

<210> SEQ ID NO 15
<211> LENGTH: 19
<212> TYPE: DNA
<213> ORGANISM: Artificial Sequence
<220> FEATURE:
<223> OTHER INFORMATION: Synthetic oligonucleotide probe

<400> SEQUENCE: 15
tcgtctaaca tagcaaatc                                                      19

<210> SEQ ID NO 16
<211> LENGTH: 36
<212> TYPE: DNA
<213> ORGANISM: Artificial Sequence
<220> FEATURE:
<223> OTHER INFORMATION: Synthetic oligonucleotide probe

<400> SEQUENCE: 16
ttctaatacg actcactata gggcaagttg tcctcc                                   36

<210> SEQ ID NO 17
<211> LENGTH: 36
<212> TYPE: DNA
<213> ORGANISM: Artificial Sequence
<220> FEATURE:
<223> OTHER INFORMATION: Synthetic oligonucleotide probe

<400> SEQUENCE: 17
tgaaattaac cctcactaaa gggacgtggt cagcgt                                   36
```